(12) United States Patent
Pettit et al.

(10) Patent No.: US 7,705,188 B2
(45) Date of Patent: Apr. 27, 2010

(54) STRUCTURAL MODIFICATION OF RESVERATROL: SODIUM RESVERASTATIN PHOSPHATE

(75) Inventors: George R. Pettit, Paradise Valley, AZ (US); Matthew P. Grealish, San Diego, CA (US)

(73) Assignee: Arizona Board of Regents, a body corporate of the State of Arizona, Acting for and on Behalf of the Arizona State University, Scottsdale, AZ (US)

( * ) Notice: Subject to any disclaimer, the term of this patent is extended or adjusted under 35 U.S.C. 154(b) by 0 days.

(21) Appl. No.: 10/510,675

(22) PCT Filed: Apr. 10, 2003

(86) PCT No.: PCT/US03/11008

§ 371 (c)(1),
(2), (4) Date: Oct. 6, 2004

(87) PCT Pub. No.: WO03/086414

PCT Pub. Date: Oct. 23, 2003

(65) Prior Publication Data

US 2005/0240062 A1  Oct. 27, 2005

Related U.S. Application Data

(60) Provisional application No. 60/371,782, filed on Apr. 10, 2002.

(51) Int. Cl.
*C07C 43/20* (2006.01)
*C07F 9/09* (2006.01)

(52) U.S. Cl. .................. 568/17; 568/646; 568/654; 558/87; 558/210

(58) Field of Classification Search .................. 514/109, 514/720, 721; 568/646, 17
See application file for complete search history.

(56) References Cited

U.S. PATENT DOCUMENTS

| | | | |
|---|---|---|---|
| 6,197,834 B1 * | 3/2001 | Docherty | 514/733 |
| 6,743,937 B2 * | 6/2004 | Seyedi et al. | 558/210 |
| 2002/0028852 A1 * | 3/2002 | Ghai et al. | 514/720 |
| 2003/0118617 A1 | 6/2003 | Soby et al. | |

FOREIGN PATENT DOCUMENTS

WO  WO 01/60774 A1  8/2001

OTHER PUBLICATIONS

Orsini et al., Carbohydrate Research, vol. 301, Issue 3-4, Jun. 1997, pp. 95-109.*
International Search Report for PCT/US03/11008 dated Aug. 21, 2003.
International Preliminary Examination Report for PCT/US03/11008 dated Jul. 23, 2004.
Cushman et al., "Synthesis and Evaluation of Analogues of (Z)-1-(4-Methoxyphenyl)-2-(3,4,5-trimethoxyphenyl)ethene as Potential Cytotoxic and Antimitotic Agents", J. Med. Chem. 35:2293-2306 (1992).
Ryu et al., "Antitumor Activity of Some Phenolic Components in Plants", Arch. Pharm. Res. vol. 17, No. 1, pp. 42-44 (1994).
Takaoka, "The Synthesis of Resveratrol and Its Derivatives", Proceedings of the Imperial Academy (Tokyo), vol. 16, pp. 405-407 (1940).
Rimando et al., "Cancer Chemopreventive and Antioxidant Activities of Pterostilbene, a Naturally Occurring Analogue of Resveratrol", J. Agric. Food Chem. 50:3453-3457 (2002).
Pettit et al., "Antineoplastic Agents. 465. Structural Modification of Resveratrol: Sodium Resverastatin Phosphate", J. Med. Chem. 45:2534-2542 (2002).
Spath et al., "Constituents of red sandal wood. III. Synthesis of Pterostilbene", Ber. vol. 74B, pp. 189-192 (Feb. 1941) (Abstract attached).
Gracza et al., "High-performance liquid chromatographic separation and quantitative determination of plant stilbene derivatives", Journal of Chromatography, vol. 287, No. 2, pp. 462-465 (Apr. 1984) (Abstract attached).

* cited by examiner

*Primary Examiner*—Rosalynd Keys
(74) *Attorney, Agent, or Firm*—McAndrews, Held & Malloy Ltd.

(57) ABSTRACT

Described herein are novel compounds having antineoplastic and antimicrobial activity, obtained via structural modifications of resveratrol and combretastatin A-4, methods for synthesis of these compounds, and their use in pharmaceutical composition and for use in the treatment of mammals having cancer. Examples of the novel compounds are: (Z)- and (E)-3,4',5-trimethoxystilbene (4a, 4b); (Z)- and (E)-3,5-dimethoxy-4'-hydroxystilbene (14c, 14d); (Z)- and (E)-3-hydroxy-4',5-dimethoxystilbene (14g, 14h); (Z)- and (E)-3,5-dihydroxy-4'-methoxy-stilbene (14k, 14l); sodium resverastatin dibenzyl phosphate ((Z)-3,5-dimethoxy-4-[O-bis(benzyl)phosphoryl]-stilbene) (14m); and sodium resverastatin phosphate (14n).

5 Claims, 5 Drawing Sheets

STRUCTURAL MODIFICATION OF RESVERATROL: SODIUM RESVERASTATIN PHOSPHATE

RELATED APPLICATION DATA

This application is the U.S. national stage of PCT/US03/11008 filed on Apr. 10, 2003, which is based on and claims the benefit of U.S. Provisional Patent Application No. 60/371,782 filed on Apr. 10, 2002, which is incorporated herein in its entirety by this reference.

GOVERNMENT INTEREST

Financial assistance for this invention was provided by the United States Government, Division of Cancer Treatment and Diagnosis, National Cancer Institute, Department of Health and Human Services Outstanding Investigator Grant Numbers CA44344-05-12 and RO1 CA90441-01. Thus, the United States Government has certain rights in this invention.

FIELD OF THE INVENTION

The present invention relates generally to antineoplastic compositions. More particularly this invention relates to derivatives of resveratrol, combretastatin A-4, and methods of synthesis thereof.

BACKGROUND OF THE INVENTION

The antitumor properties of a series of structurally simple compounds derived from tropical and subtropical trees of the family Combretaceae are under ongoing investigation. The genus *Combretum* contains 25 species used in the traditional medical practices of Africa and India. The South African bush willow *Combretum caffrum* was used by the Zulu and other Southern African people as a charm to ward off enemies and in traditional medical practices.

*Combretum caffrum* (Eckl. Zehy.) Kuntze collected in 1973 and recollected in 1979 afforded extracts that showed activity in the astrocyte reversal (9ASK) and murine lymphocytic leukemia screening assays of the National Cancer Institute of the U.S.A. Historically, this extract was the first to be successfully fractionated by means of the 9ASK system. In 1982 the isolation of the first member of the combretastatin series was disclosed. Also disclosed was its structure and later synthesis. (Pettit, G. R., et al., Isolation and Structure of Combretastatin, *CAn. J. Chem.* 1982, 60, 1374-1376; Pettit, G. R., et al., Synthesis of Natural (−)-combretastatin, *J. Org. Chem.* 1985, 50, 3404-3406.) Subsequently, a number of additional cancer cell line active constituents were isolated. These investigations eventually led to applicant's isolation, structure and synthesis of the cis-stilbene combretastatin A-4 (2a) and its phosphate prodrug (2b). (Pettit, G. R., et al., Isolation and Structure of the Strong Cell Growth and Tubulin Inhibitor Combretastatin A-4, *Experentia,* 1989, 45, 209-211; Pettit, G. R., et al., Antineoplastic agents 291. Isolation and Synthesis of Combretastatin A-4, A-5, and A-6, *J. Med. Chem.* 1995, 38, 1666-1672; Ndayikengurukiye, H., et al., Alkoxylated p-phenylenevinylene Oligomers: Synthesis and Spectroscopic and Electrochemical Properties, *Tetrahedron* 1997, 53, 13811-13828.) The latter has been shown to selectively damage tumor neovasculature with induction of extensive blood flow shutdown in the metastatic tumor compared to normal tissues.

For example, six hours following treatment using the murine CaNT adenocarcinoma and a single i.p. injection of combretastatin A-4 prodrug (100 mg/kg), vascular function shutdown in the tumor was rapid, irreversible and extensive (8). (Ndayikengurukiye, H., et al., Alkoxylated p-phenylenevinylene Oligomers: Synthesis and Spectroscopic and Electrochemical Properties. *Tetrahedron* 1997, 53, 13811-13828.) In November 1998 four Phase I human cancer trials were initiated, two in the United States and two in England. Current clinical trials (9) have been encouraging and Phase II human cancer clinical trials have been or will be initiated soon. (Cushman, M., et al., Synthesis and Evaluation of Analogues of (Z)-1-(4-methoxyphenyl)-2-(3,4,5-trimethoxyphenyl) ethane as Potential Cytotoxic and Antimitotic Agents, *J. Med. Chem*-1992, 35, 2293-2306.)

The need for such compounds is both critical and ongoing. The isolation of such valuable compounds is the purpose of the present invention.

BRIEF SUMMARY OF THE INVENTION

Resveratrol (1), 3,4',5-trihydroxy-trans-stilbene, is a phytoalexin found in grapes and certain other plants. (Orsini, F., et al., Isolation, Synthesis, and Antiplatelet Aggregation of Resveratrol 3-O-β-D-glucopyranoside and Related Compounds, *J. Nat. Prod.* 1997, 60, 1082-1087; Siemann, E. H., et al., Concentration of the Phytoalexin Resveratrol in Wine, *Amer. J. of Enology and Viticulture* 1992, 43, 49-52; Goldberg, D., et al., A Global Survey of Trans-resveratrol Concentrations in Commercial Wines, *Clin. Chem.* 1995, 46, 159-1665; Adesanya, S. A., et al., Stilbene Derivatives from *Cissus quandrangularis. J. Nat. Prod.* 1999, 62, 1694-1695; Arichi, H., et al., Effects of Stilbene Components of the Root of *Polygonum cuspidatum* Sieb. Et Zucc. On Lipid Metabolism, *Chem. and Pharm. Bull.* 1982, 30, 1766-1770; Ingham, J., 3,5,4'-trihydroxystilbene as a Phytoalexin from Groundnuts (*Arachis hypogaea*). *Phytochem.* 1976, 15, 1791-1793.)

The compound exhibits a variety of useful biological properties including antileukemic, antibacterial, antifungal, antiplatelet aggregation, and coronary vasodilator activities. (Jeandet, P., et al., The Production of Resveratrol by Grape Berries in Different Developmental Stages, *Am J. of Enology and Viticulture* 1991, 42, 41-46; Manila, E., et al., Anti-leukaemic compounds Derived from Stilbenes in *Picea abies* Bark, *Phytochem.* 1993, 33, 813-816; Kubo, M., et al., *Shoyayugaku Zasshi* 1981, 35, 58; Creasy, L., et al., Phytoalexin Production Potential of Grape Berries, *J. of the Am. Soc. of Horticultural Science* 1988, 113, 230-234; Langcake, C., et al., Identification of Pterostilbene as a Phytoalexin from *Vitis vinifera* Leaves, *Phytochemistry* 1979, 18, 1025-1027; Langcake, R., et al., The Relationship of Resveratrol Production to Infection of Grapevine Leaves by *Botrytis cenerea, Vitis* 1979 18:244-253; Chung, M., et al., An Antiplatelet Principle of *Veratrum formosanum, Planta Medica* 1992, 58, 274-276; Inamori, Y., et al., The Ichthyotoxicity and Coronary Vasodilator Action of 3,3'-dihydroxy-α,β-diethylstilbene, *Chem. Pharm. Bull.* 1987, 35, 887-890.) This triphenolic stilbene (1) also has strong antioxidative and anti-inflammatory activities associated with chemopreventive properties. (Pattichis, K, et al., Inhibition of Human LDL Oxidation by Resveratrol, *Lancet* 1993, 1103-1108; Goldberg, D., More on Antioxidant Activity of Resveratrol in Red Wine, *Clin. Chem.* 1996, 42, 113-114; Pace-Asciak, C., et al., The Red Wine Phenolics Trans-resveratrol and Quercetin Block Human Platelet-Aggregation and Eicosanoid Synthesis-implications for Protection Against Coronary Heart-Disease, *Clinical Chemica Acta* 1995, 235, 207=219.) Resveratrol (1) has been suggested as a possible cancer chemopreventive agent based on inhibitory effects on tumor initiation, promotion, and progression. (Jang, M., et al., Cancer Chemopreventive Activity of Resveratrol. A natural product Derived from Grapes, *Science* 1997, 275, 218-220; Uenobe, F., Antimutagenic Effects of Resveratrol Against Trp-P-1, *Mutation Res.* 1997, 373, 197-200.)

In addition to antitumor promoting activity, resveratrol (1) has displayed cancer cell growth inhibition in vitro. (Chanvitayapongs, S., et al., Amelioration of Oxidative Stress by Antioxidants and Resveratrol in PC12 cells, *NeuroReport* 1997, 8, 1499-1502; Mgbonyebi, O., et al., Antiproliferative Effect of Synthetic Resveratrol on Human Breast Epithelial Cells, *Int. J. Oncol.* 1998, 12, 865-869; Jayatilake, G., et al., Kinase Inhibition From *polygonum cuspidatum* 1993, 56, 1805-1810; Chun, Y., et al., Resveratrol is a Selective Human Cytochrome P450 1A1 inhibitor, *Biochem. Biophys. Res.* 1999, 262, 20-24.) Importantly, resveratrol (1) has recently been shown to induce apoptosis and decrease expression of Bcl-2 in the human leukemia HL-60 cell line. (Surh, Y. J., et al., Resveratrol, an Antioxidant Present in Red Wine, Induces Apoptosis in Human Promyelocytic Leukemia (HL-60) cells, *Cancer Lett.* 1999, 140, 1-10.) Furthermore, the resveratrol tetramers vatdiospyridol and resveratrol oligomers recently isolated from Asian plants have shown significant inhibition of the growth of several cancer cell lines. (Seo, H., et al., Resveratrol Tetramers from *Vatica Diospyoides*. *J. Org. Chem.* 1999, 64, 6976-6983; Ohyama, M., et al., Antitumor Agents 200. Cytotoxicity of Naturally Occurring Resveratrol Oligomers and their Acetate Derivatives, *Bioorg. Med. Chem. Lett.* 1999, 9, 3057-3060.) Other biological properties of resveratrol (1) include activities targeting cyclooxygenase, tyrosine kinase (PTK), and protein kinase C (PKC), as well as selective human cytochrome P450 1A1 inhibition and microbiological transformation to resveratrol 3-O-β-D-glucoside. (Jang, M., et al., Cancer Chemopreventive Activity of Resveratrol. A Natural Product Derived from Grapes, *Science* 1997, 275, 218-220; Jayatilake, G., et al., Kinase Inhibition from *Polygonum cuspidatum*, *J. Nat. Prod.* 1993, 56, 1805-1810; Chun, Y., et al., Resveratrol is a Selective Human Cytochrome P450 1A1 Inhibitor, *Biochem. Biophys. Res.* 1999, 262, 20-24; Cichewicz R. H., et al., Biotransformation of resveratrol to piceid by *Bacillus cereus*, *J. Nat. Prod.* 1998, 61, 1313-1314.)

The compounds in question were isolated/synthesized in the manner generally described below. These compounds were discovered to have the properties noted.

Accordingly the prime object of the present invention was to discover pharmaceutically active derivatives of resveratrol.

Another object of the present invention was to discover pharmaceutically active derivatives of combretastatin A-4.

DESCRIPTION OF THE PREFERRED EMBODIMENTS

Figure 1:
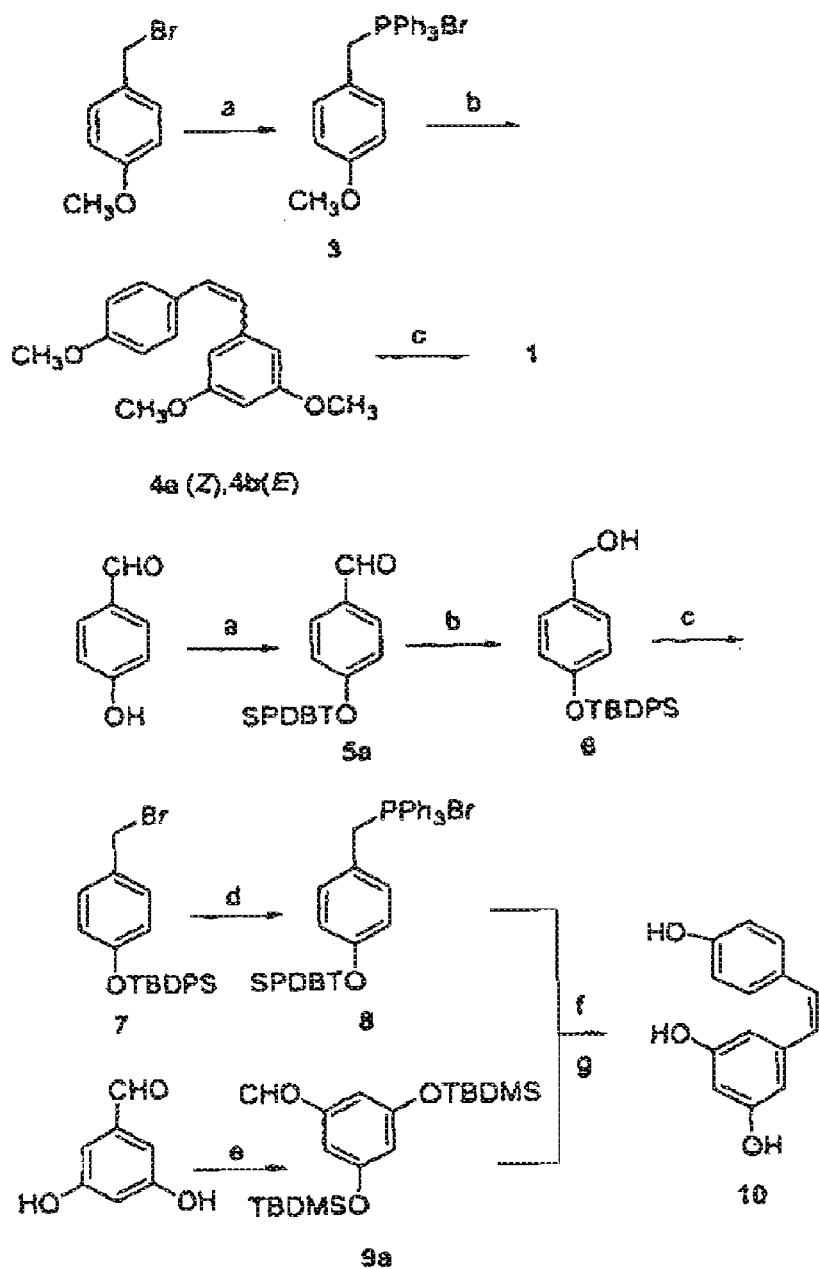
FIG. 1. Reaction scheme for production of cis-resveratrol (10).
Figure 2:
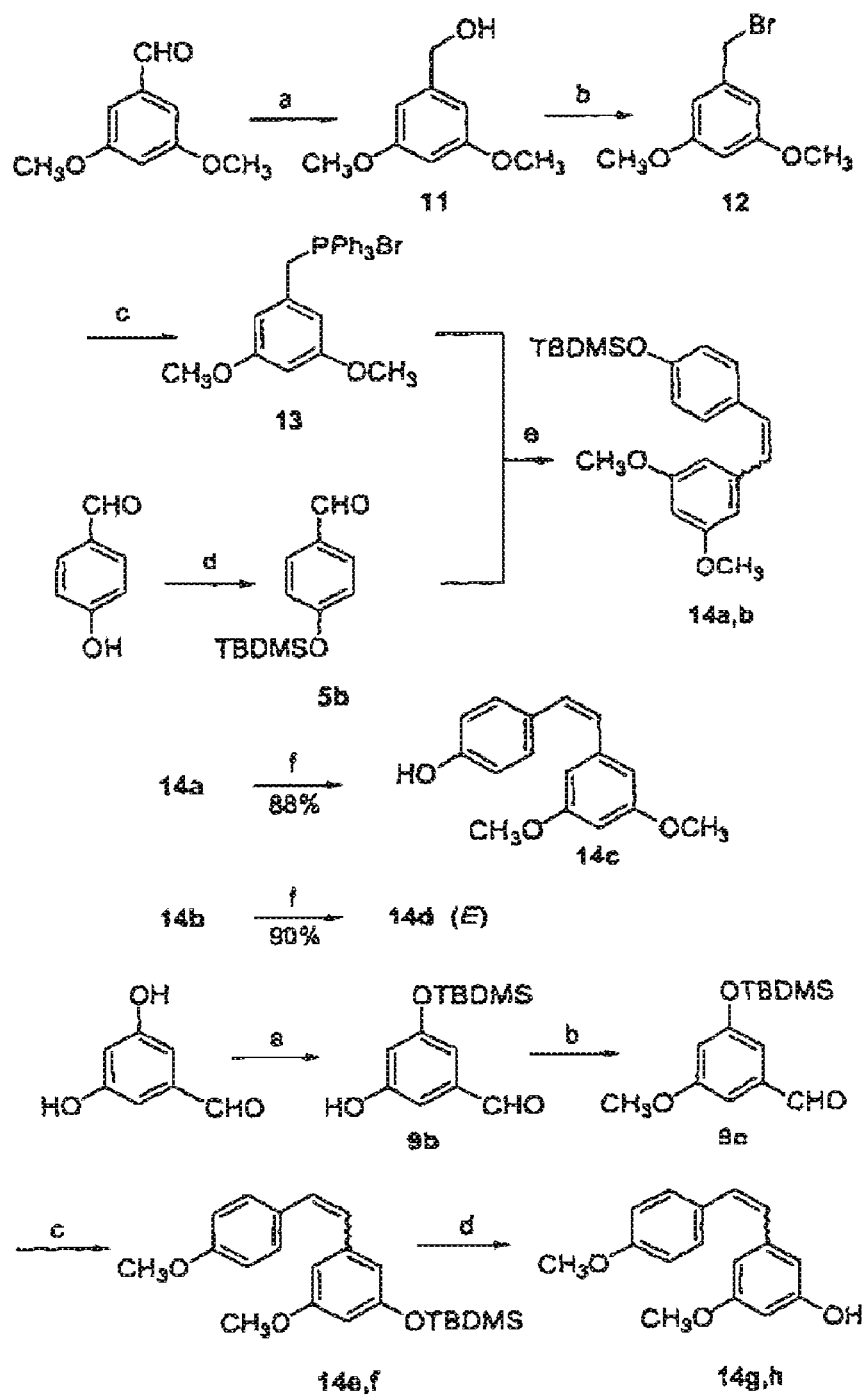
FIG. 2. Reaction scheme for production of 3-hydroxy-4', 5-dimethoxystilbene (14g,h).
Figure 3:
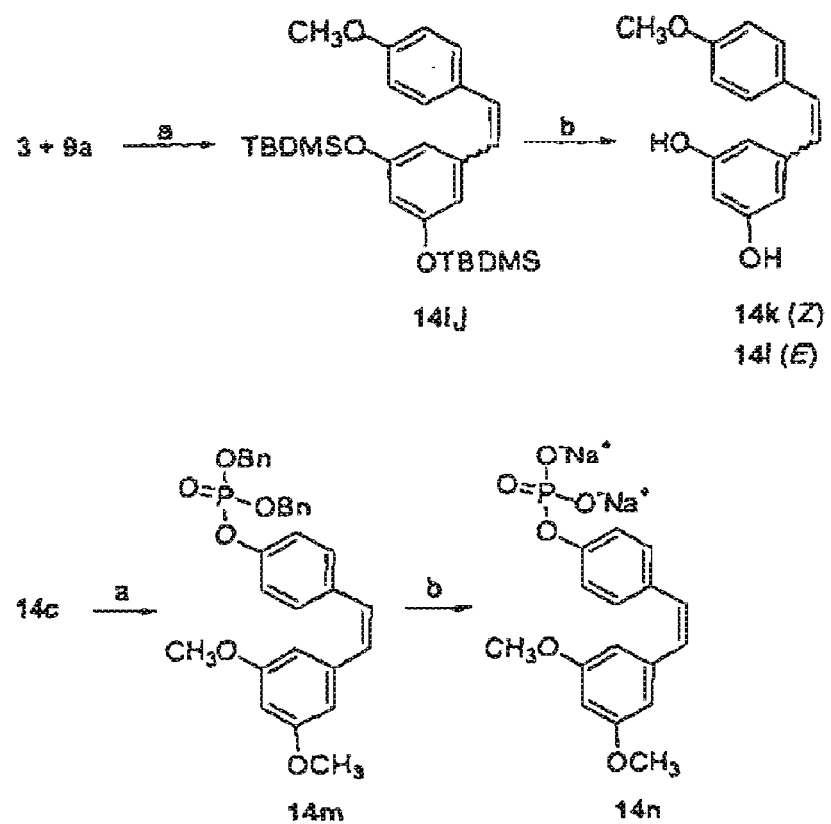
FIG. 3. Reaction scheme for production of sodium resverastatin phosphate (14n).
Figure 4:
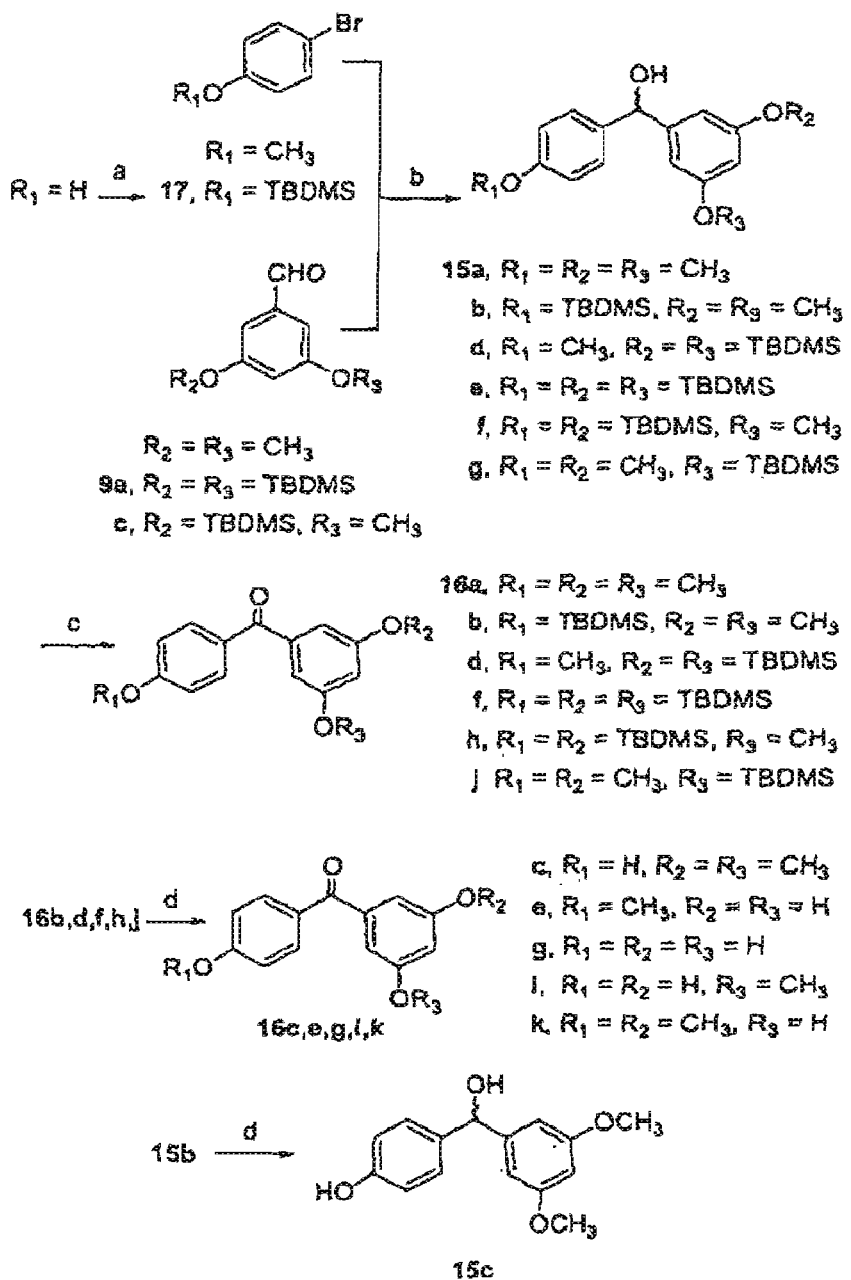
FIG. 4. Reaction scheme for production of 4'-hydroxy-3, 5-dimethoxybenzhydrol (15c).
Figure 5:
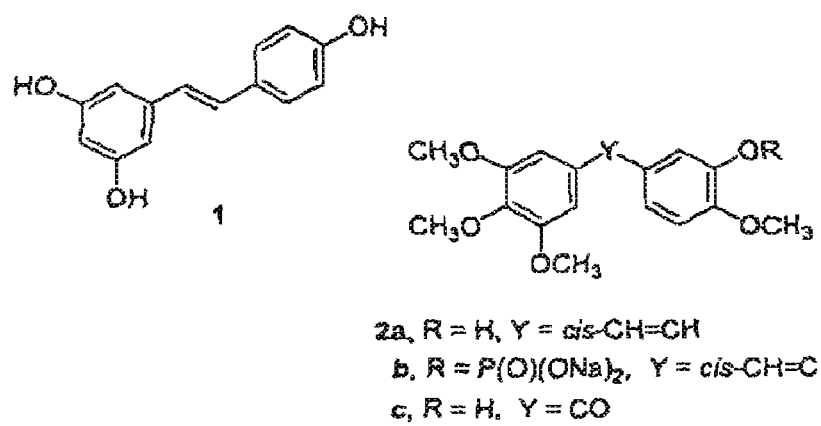
FIG. 5. Chemical structures of resveratrol (1), combretastatin A-4 (2a), combretastatin A-4 sodium phosphate prodrug (2b), and phenstatin (2c).

The compounds discovered were obtained in the following manner, using the following lexicon that should be familiar to one of ordinary skill in the art.

All solvents were redistilled. Hunig's base and proton sponge refer respectively to N,N,-diisopropylethylamine and 1,8-bis-(dimethylamino)-naphthalene. Both the course and products from reactions were monitored by thin-layer chromatography using Analtech silica gel GHLF uniplates. All reactions were carried out under an inert atmosphere. Solvent extracts of aqueous solutions were dried over anhydrous sodium sulfate unless otherwise noted. Flash column chromatography was performed using silica gel (230-400 mesh ASTM).

Melting points were recorded employing an Electrothermal 9100 digital melting point apparatus and are uncorrected. The IR spectra were obtained using a Mattson FTIR model 2020 instrument. Low-resolution mass spectral data were collected using a Varian MAT 312 instrument (EIMS). The high-resolution FAB spectra were obtained employing a Kratos MS-50 spectrometer. All $^1$H and $^{13}$C-NMR spectra were determined using a Varian Gemini 300 MHz instrument with CDCl$_3$ (TMS internal reference) as solvent unless otherwise noted. The $^{31}$P-NMR spectra were measured in CDCl$_3$ with 85% H$_3$PO$_4$ as an external standard employing a Varian Unity 500 MHz instrument.

The following schemes and structural formulae of identified compounds, set forth at the end of this application, were used. Where practical general procedures for certain classes of compounds are also set forth below.

A starting material in stilbene synthesis is 4-methoxybenzyltriphenylphosphonium bromide (3) that was obtained as follows: To a solution of 4-methoxybenzyl bromide (22.4 g) in toluene (200 ml) was added triphenylphosphine (29.2 g). The solution was heated at reflux for 12 hours under argon. The resulting precipitate was collected and recrystallized from ethanol as colorless crystals (44.0 g, 85.3%) mp 235-237° C., (lit[19] mp 234° C.).

The general procedure for the stilbene syntheses was as follows. To the phosphonium bromide (1-35 mmol) in anhydrous tetrahydrofuran (5-200 ml) at −78° C. was added n-butyl lithium (2.44 M, 1.0 equiv.), and the resulting red solution was stirred under argon for 2-4 hours. A solution of the aldehyde (1.0 equiv.) in tetrahydrofuran was added dropwise over 30 minutes and the mixture stirred for 6-15 hours. The resulting cream suspension was poured into water and extracted with dichloromethane. The organic phase was washed with water and removal of the solvent in vacuo afforded a tan oil. The oil was separated by flash column chromatography (49:1 hexane:ethyl acetate). The cis stilbene eluted first as a clear oil followed by the trans isomer as a colorless sold or oil (TBDMS protected).

By following the above general procedure, 3,4',5-trimethoxystilbene (4a,b) was obtained in the following manner. Reaction of phosphonium bromide (12.5 g) (3) and 3,5-dimethoxybenzaldehyde (4.5 g) led to cis stilbene (4a) as a clear oil (3.56 g) and the trans isomer (4b) as a colorless sold (3.08 g), 91% total yield: (Z) isomer (4a) IR neat, cm$^{-1}$ v$_{max}$ 3449, 2957, 2836, 1591, 1250, 1065, 640; $^1$H-NMR δ 6.22 (2H, dd, J=2.4, 8.7 Hz), 6.77 (2H, dd, J=2.4, 8.7 Hz), 6.53 (1H, d, J=12.0 Hz), 6.45 (1H, d, J=12.0 Hz), 6.44 (2H, d, J=2.1 Hz), 6.32 (1H, t, J=2.1 Hz), 3.78 (3H, s, OCH$_3$), 3.67 (6H, s, OCH$_3$×2); (E) isomer (4b) mp 57-58° C., (lit[20] mp 55-56° C.).

Resveratrol (1) was obtained from a stilbene in the following manner. To stilbene 4b (3.1 g) in anhydrous dichloromethane (150 ml) at −78° C. was added (dropwise) boron tribromide (1.0 M, 34.5 ml), and the resulting red solution was stirred under argon for 30 minutes. The solution was poured into water and extracted with dichloromethane. The organic phase was washed with water and removal of the solvent in vacuo afforded a tan oil, which was separated by flash column chromatography (1:1/hexane:ethyl acetate) to afford a colorless sold (2.26 g, 86%): mp 260° C. (lit[12c] mp 260° C.).

The compound 4-(tert-butyldiphenylsilyloxy)-benzaldehyde (5a) was obtained in the following manner. To a solution of 4-hydroxybenzaldehyde (3.2 g) in dimethylformamide (50 ml) was added imidazole (1.9 g, 1.1 equiv.). The solution was stirred for 15 minutes, tert-butyldiphenylsilyl chloride (7.4 ml, 1.1 equiv.) was added, and the light brown solution was stirred for 3 hours. The reaction mixture was poured into water and extracted with ethyl acetate. Removal of the solvent in vacuo from the organic phase provided a brown oil. The oil was separated by flash column chromatography (1:0→19:1 hexane:ethyl acetate) to afford the aldehyde (5a) as a colorless solid (6.4 g, 68%): mp 103-105° C. IR (neat, cm$^{-1}$) $v_{max}$ 3399, 2932, 2859, 1699, 1599, 1506, 1273, 1157, 910; $^1$H-NMR δ 9.80 (1H, s, CHO), 7.69 (4H, m, Ar—H), 7.64 (2H, d, J=8.7 Hz), 7.40 (6H, m, Ar—H), 6.86 (2H, d, J=8.7 Hz), 1, 11 (9 Hm sm C(CH$_3$)$_3$), Anal. (C$_{23}$H$_{24}$O$_2$Si) C, H.

The compound 4-(tert-butyldiphenylsilyloxy)-benzyl alcohol (6) was obtained in the following manner. To a solution of aldehyde 5a (4.7 g) in methanol (100 ml) at 0° C. was slowly added sodium borohydride (0.59 g, 1.2 eq.). After stirring for 2 hours the reaction mixture was poured into water, solvent reduced to a minimum, extracted with ethyl acetate and the solvent removed in vacuo to give 4.1 g of a clear oil (88%); IR (neat, cm$^{-1}$) $v_{max}$ 3346, 2932, 2859, 1609, 1510, 1427, 1256, 1113, 918; $^1$H-NMR δ 7.72 (4H, m, Ar—H), 7.39 (6H, m, Ar—H), 7.10 (2H, d, J=8.7 Hz), 6.76 (2H, d, J=8.7 Hz), 4.55 (2H, s, CH$_2$), 1.11 (9H, s, C(CH$_3$)$_3$). Anal. (C$_{23}$H$_{26}$O$_2$Si) C, H.

The following procedure was used to obtain 4-(tert-butyldiphenylsilyloxy)-benzyl bromide (7). Phosphorus tribromide (0.5 ml) was slowly added to a solution of the alcohol 6 (4.0 g) in dichloromethane (75 ml) at 0° C., and stirring was continued for 12 hours. The reaction mixture was poured into aqueous sodium bicarbonate, extracted with dichloromethane and the solvent removed in vacuo to afford 4.3 g of a colorless solid (89%): EIMS m/z 426 (M+, [81]Br), 424 (M+[79]Br), 390, 369, 367, 345, 289, 135: IR (neat, cm$^{-1}$) $v_{max}$ 3397, 3073, 2932, 2859, 1607, 1510, 1427, 1263, 1113, 918; $^1$H-NMR δ 7.72 (4H, m, Ar—H), 7.39 (6H, m, Ar—H), 7.13 (2H, d, J=8.4 Hz) 6.72 (2H, d, J=8.4 Hz), 4.42 (2H, s, CH$_2$), 1.11 (9H, s, C(CH$_3$)$_3$). $^{13}$C-NMR (75.5 MHz) δ 155.6, 135.4, 132.4, 130.1, 129.9, 127.7, 119.9, 34.0, 26.5, 19.5. Anal. (C$_{23}$H$_{25}$BrOSi) C, H.

The compound 4-(tert-butyldiphenylsilyloxy)-benzyltriphenylphosphonium bromide (8) was obtained in the following manner. To a solution of bromide (7) (4.3 g) in toluene (100 ml) was added triphenylphosphine (13.2 g). After heating at 100° C. for 2 hours, the reaction mixture was cooled to room temperature, and the product was collected and recrystallized from ethanol to yield 6.1 g of a colorless solid (89%) mp 233° C.; FABMS m/z 607.2583 (M+—Br), IR (neat, cm$^{-1}$) $v_{max}$ 3385, 3054, 2934, 2859, 2787, 1607, 1512, 1437, 1273, 1111, 924; $^1$H-NMR δ 7.61 (19H, m, Ar—H), 7.30 (6H, m, Ar—H), 6.76 (2H, dd, J=2.4, 8.7 Hz) 6.51 (2H, d, J=8.7 Hz), 5.18 (2H, s, CH$_2$), 1.04 (9H, s, C(CH$_3$)$_3$). $^{13}$C-NMR (75.5 MHz) δ 155.7, 135.3, 134.7, 134.7, 134.3, 132.3, 132.3, 130.0, 129.8, 127.6, 120.2, 120.1, 118.9, 118.9, 118.1, 117.3, 30.5, 30.1, 26.5, 19.4. Anal. (C$_{41}$H$_{40}$BrOSi) C, H.

The compound 3,5-di(tert-butyldimethylsilyloxy)-benzaldehyde (9a) was obtained in the following manner. DIEA (7.7 ml, 2 equiv.) was added to a solution of 3,5-dihydroxybenzaldehyde (3.0 g) in dimethylformamide (30 ml), and the solution was stirred for 15 minutes. The silyl chloride (7.5 g) was added and the light brown solution stirred for 16 hours. The mixture was poured into water and extracted with dichloromethane. Removal of the solvent in vacuo yielded a brown oil that was separated by flash column chromatography (9:1 hexane:ethyl acetate) to yield the disilylether as a tan oil (7.6 g, 94%): EIMS m/z 366 (M+), 309, 267, 239, 133, 73; IR (KBr, cm$^{-1}$) $v_{max}$ 2957, 2861, 2805, 2710, 1705, 1385, 831; $^1$H-NMR δ 9.85 (1H, s, CHO), 6.95 (2H, d, J=2.1 Hz), 6.58 (1H, t, J=2.1 Hz), 0.99 (18H, s, C(CH$_3$)$_3$×2), 0.22 (12H, s, Si(CH$_3$)$_2$×2).

The compound identified as cis-Resveratrol (10) was obtained as follows:

the Wittig reaction was performed as summarized above using 5 mmol of phosphonium salt, and the TBDPS-protected stilbene isomers were isolated as a mixture. The mixture was dissolved in tetrahydrofuran and treated with TBAF (3.0 eq), being stirred for 1 hour. The product was purified by gravity column chromatography (3:2 hexane:ethyl acetate) and yielded 0.21 g of the cis-isomer as a colorless solid and 0.24 g of a mixture of isomers (95.1%): mp 172-174° C. (lit[12c] mp 170-174° C.).

Hunig's base (10.2 ml, 2 eq) was added to a solution of 4-hydroxybenzaldehyde (6.0 g) in dimethylformamide (50 ml) to obtain 4-(tert)-butyldimethylsilyloxy-benzaldehyde (5b). The solution was stirred for 15 minutes, tert-butyldimethylsilyl chloride (8.9 g) was added, and the clear light brown solution was stirred for 15 hours. The reaction mixture was poured into water, extracted with dichloromethane and the solvent removed in vacuo to afford a brown oil. The oil was separated by vacuum distillation to yield aldehyde 5b as a colorless oil (8.4 g, 73%): IR (neat, cm$^{-1}$) $v_{max}$ 3385, 2932, 2859, 1699, 1599, 1508, 1273, 1155, 909; $^1$H-NMR δ 9.88 (1H, s, CHO), 7.79 (2H, d, J=8.4 Hz), 6.94 (2H, d, J=8.4 Hz), 0.98 (9H, s, C(CH$_3$)$_3$), 0.25 (6H, s, Si(CH$_3$)$_2$). Anal. (C$_{13}$H$_2$O$_2$Si) C, H.

To obtain 3,5-dimethoxybenzyltriphenylphosphonium bromide (13) 3,5-dimethoxybenzaldehyde (10 g) in methanol was reduced with sodium borohydride, the oily product 11, (9.6 g, 93% yield) was treated (0°, 12 hours) with phosphorous tribromide (2.7 ml), and to its resulting bromide 12 (11.6 g, 89%) in toluene (200 ml) was added triphenylphosphine (13.2 g). After heating at reflux for 12 hours the mixture was cooled to room temperature. The product was collected and recrystallized from ethanol to yield 22.8 g of a colorless solid (92%) mp 275° C., lit[12c] mp 266-268° C.; $^1$H-NMR δ 7.70 (15H, m), 6.33 (2H, d, J=2.1 Hz), 6.30 (1H, t, J=2.1 Hz), 5.30 (2H, d, J=14.4 Hz), 3.53 (6H, s, OCH$_3$×2).

To obtain 4'-(tert-butyldimethylsilyloxy)-3,5-dimethoxystilbene (14a,b), phosphonium bromide 13 (6.9 g) in anhydrous tetrahydrofuran (40 ml) at 78° C. was treated with n-butyl lithium 2.5 M, 5.6 ml) and aldehyde 5b (3.3 g) in tetrahydrofuran (10 ml) according to the general Wittig-stilbene procedure (see above). (Z)-isomer (14a): EIMS m/z 370 (M+), 355, 313, 298, 157; IR (KBr, cm$^{-1}$) $v_{max}$ 2932, 2857, 1591, 1508, 1262, 1155, 914; $^1$H-NMR δ 7.14 (2H, d, J=8.5 Hz), 6.70 (2H, d, J=8.5 Hz), 6.51 (1H, d, J=12.0 Hz), 6.43

(1H, d, J=12.0 Hz), 6.42 (2H, d, J=2.0 Hz), 6.31 (1H, t, J=2.0 Hz), 3.65 (6H, s, OCH$_3$×2), 0.96 (9H, s, C(CH$_3$)$_3$), 0.17 (6H, s Si(CH$_3$)$_2$); $^{13}$C-NMR (75.5 MHz) δ 160.51, 154.87, 139.40, 130.27, 130.21, 128.76, 119.77, 106.57, 99.81, 55.17, 25.65, 18.22, −4.45. Anal. (C$_{22}$H$_{30}$O$_3$Si) C, H. (E) isomer (14b): EIMS m/z 370 M+), 355, 313, 255 165 73; IR (KBr, cm$^{-1}$) ν$_{max}$ 2955, 2859, 1595, 1508, 1263, 1154, 914, 839; $^1$H-NMR δ 7.40 (2H, d, J=8.5 Hz). 7.05 (1H, d, J=16.0 Hz), 6.92 (1H, d, J=16.0 Hz), 6.85 (2H, d, J 8.5 Hz), 6.66 (2H, d, J=2.5 Hz), 6.39 (1H, t, J=2.5 Hz), 3.84 (6H, s, OCH$_3$×2), 1.01 (9H, s, C(CH$_3$)$_3$), 0.23 (6H, s, Si(CH$_3$)$_2$); $^{13}$C-NMR (75.5 MHz) δ 160.9, 155.7, 139.7, 130.5, 128.8, 127.7, 126.7, 120.3, 104.3, 99.6, 55.3, 25.7, 18.2, −4.4. Anal. (C$_{22}$H$_{30}$O$_3$Si) C, H.

(Z) and (E)-3,5-dimethoxy-4'-hydroxy-stilbene (14c and d) and General Silyloxy Deportation Procedure were performed as follows. To a solution of the silyloxy protected (Z)-stilbene (14a, 1.2 g) in anhydrous tetrahydrofuran (20 ml) was added tetrabutylammonium fluoride (1 M, 3.4 ml). The clear light yellow solution was stirred for 45 minutes, poured into water, extracted with dichloromethane and the solvent removed in vacuo to provide a tan oil. The oil was separated by gravity column chromatography (4:1 hexane-ethyl acetate) to afford cis stilbene 14c as a yellow oil (88%): IR (neat, cm$^{-1}$) ν$_{max}$ 3385, 3005, 2940, 2837, 1591, 1512, 1456, 1152 1065, 679; $^1$H-NMR δ 8.01 (1H, s, OH), 7.15 (2H, d, J=8.7 Hz), 6.71 (2H, d, J=8.7 Hz). 6.51 (1H, d, J=12.6 Hz), 6.43 (2H, d, J=2.5 Hz), 6.42 (1H, d, J=12.6 Hz), 6.31 (2H, d, J=2.5 Hz), 3.66 (6H s, OCH$_3$×2). Anal. (C$_{16}$H$_{16}$O$_3$) C, C, H. (E)-3,5-dimethoxy-4'-hydroxy-stilbene (14d) was similarly prepared from stilbene 14b (0.5 g) and tetrabutyl-ammonium fluoride (1M, 1.3 ml) in anhydrous tetrahydrofuran (10 ml) was added to yield 0.8 g of yellow oil (90%): IR (neat, cm$^{-1}$) ν$_{max}$ 3385, 3005, 2940, 2837, 1591, 1512, 1456, 1152, 1065, 961; $^1$H-NMR δ 8.01 (1H, s, OH), 7.44 (2H, d, J=8.7 Hz), 7.18 (1H, d, J=16.5 Hz), 6.98 (1H, d, J=16.5 Hz), 6.85 (2H, d, J=8.7 Hz), 6.73 (2H, d, J=2.1 Hz), 6.38 (1H, t, J=2.1 Hz), 5.25 (1H, bs, OH), 3.81 (6H, s, OCH$_3$×2).

Unless otherwise noted the following intermediates and stilbene objectives were prepared by the preceding general methods for silyloxy protection, Wittig reaction and deprotection. The following procedure was followed to obtain 3-(tert-butyldimethylsilyloxy)-5-hydroxybenzaldehyde (9b). 3,5-dihydroxybenzaldehyde (1.1 g) in dimethylformamide (10 ml) was monosilylated using DIEA (1.9 ml, 1.4 equiv.) and the silyl chloride (1.2 g) with stirring for 3 hours. The oily product was separated by flash column chromatography (9:1 hexane:ethyl acetate) afford some disilylated product (0.7 g) and the desired monosilylated product as a colorless oil (0.8 g, 38.5%) that crystallized from ethanol: mp=79.6-80° C.; EIMS m/z 252 (M+), 195, 167, 58, 45; IR (KBr, cm$^{-1}$) ν$_{max}$ 3211, 2930, 2859, 1672, 1591, 1332, 841; $^1$H-NMR δ 9.84 (1H, s, CHO), 6.99 (1H, dd, J=2.0, 1.0 Hz), 6.91 (1H, dd, J=2.0, 1.0 Hz), 6.64 (1H, t, J=2.0 Hz), 6.00 (1H, bs, OH), 0.97 (9H, s, C(CH$_3$)$_3$), 0.21 (6H, s, Si(CH$_3$)$_2$); $^{13}$C-NMR (75.5 MHz) δ 192.4, 157.6, 157.4, 138.3, 114.4, 114.0, 109.1, 25.6, 18.2, −4.47. Anal. (C$_{13}$H$_{20}$O$_3$Si) C, H Also, 3-(tert-butyldimethylsilyloxy)-5-methoxybenzaldehyde (9c) was obtained in a like manner. To a solution of phenol 9b (0.7 g) in dichloromethane (10 ml) was added molecular sieves (4 Å, 0.8 g), proton sponge (1.6 g, 2.5 eq.), and trimethyloxonium tetrafluoroborate (1.1 g, 2.5 eq), and the solution was stirred for 15 hours. The solution was filtered, the sieves were rinsed with ethyl acetate and the solvent was removed from the combined filtrate in vacuo to yield a yellow oil. The oil was purified by flash column chromatography (10:1 hexane:ethyl acetate), yielding a colorless oil (0.6 g, 79%): EIMS m/z 266 (M+), 209, 181, 166, 89, 58, IR (KBr, cm$^{-1}$) ν$_{max}$ 2932, 2859, 1703, 1593, 1468, 1337, 1059, 839; $^1$H-NMR δ 9.86 (1H, s, CHO), 7.00 (1H, d, J=2.0 Hz), 6.92 (1H, d, J=2.0 Hz), 6.63 (1H, t, J=2.0 Hz), 3.81 (3H, s, OCH$_3$), 0.97 (9H, s, C(CH$_3$)$_3$), 0.21, (6H, Si(CH$_3$)$_2$); $^{13}$C-NMR (75.5 MHz) δ 191.8, 161.2, 157.3, 138.4, 114.5, 113.0, 106.6, 55.5, 25.6, 18.2, −4.5. Anal. (C$_{14}$H$_{22}$O$_3$Si) C, H.

In addition, 3-(tert-butyldimethylsilyloxy)-5,4'-dimethoxy-stilbene (14e and 14f) was obtained in a similar fashion. Reacting phosphonium bromide 8 (1.71 g) with aldehyde 9c (1.0 g) led to stilbenes 14e and 14f (0.75 g, 55% total yield). (Z)-isomer (14e): EIMS m/z 370 (M+), 313, 298, 156, 89; IR (KBr, cm$^{-1}$) ν$_{max}$ 2955, 2859, 1588, 1510, 1433, 1252, 1159, 1034, 839, 679; $^1$H-NMR δ 7.21 (2H, d, J=9.0 Hz), 6.77 (2H, d, J=9.0 Hz), 6.52 (1H, d, J=12.0 Hz), 6.45 (1H, s) 6.43 (1H d, J=12.0 Hz), 6.36 (1H, d, J=2.1 Hz), 6.27 (1H, t, J=2.1 Hz), 3.78 (3H, s, OCH$_3$), 3.67 (3H, s, OCH$_3$), 0.95 (9H, s, C(CH$_3$)$_3$), 0.11 (6H, s, Si(CH$_3$)$_2$); $^{13}$C-NMR (75.5 MHz) (75.5 MHz) δ 160.6, 158.8, 156.7, 139.4, 130.3, 128.8, 127.5, 126.3, 113.6, 110.9, 105.4, 55.2, 25.3, 14.1, −4.5. Anal. (C$_{22}$H$_{30}$O$_3$Si) C, H. (E)-isomer (14f): EIMS m/z 370 (M+), 313, 298, 156, 89; IR (KBr, cm$^{-1}$) ν$_{max}$ 2955, 2859, 1588, 1510, 1433, 1252, 1159, 1034, 941, 839; $^1$H-NMR δ 7.45 (2H, d, J=8.7 Hz), 7.01 (1H, d, J=15.9 Hz), 6.90 (2H, d, J=8.7 Hz), 6.87 (1H, d, J=15.9 Hz), 6.66 (1H, s), 6.58 (1H, s), 6.31 (1H, t, J=2.1 Hz), 3.83 (3H, s, OCH$_3$), 3.81 (3H, s, OCH$_3$), 1.00 (9H, s, C(CH$_3$)$_3$), 0.23 (6H, s, Si(CH$_3$)$_2$); $^{13}$C-NMR (75.5 MHz) δ 160.8, 159.4, 156.9, 139.6, 130.0, 128.5, 127.8, 126.6, 114.1, 110.9, 104.8, 55.3, 25.7, 14.1, −4.4. Anal. (C$_{22}$H$_{30}$O$_3$Si) C, H.

A similar process was followed to obtain 3-hydroxy-4',5-dimethoxystilbene (14g and 14h). The preceding stilbene (0.75 g) isomeric mixture was deprotected and the products separated by gravity column chromatography (9:1 hexane: ethyl acetate). As usual the cis-stilbene (0.25 g) eluted first followed by the trans-isomer (0.26 g, 99% total yield): (Z)-isomer (14g): EIMS m/z 256 (M+), 225, 181, 152, 115; IR (KBr, cm$^{-1}$) ν$_{max}$ 3407, 3005, 2938, 2837, 1607, 1511, 1456, 1300, 1254, 1154, 1057, $^1$H-NMR δ 7.20 (2H, d, J=9.0Hz), 6.77 (2H, d, J=9.0 Hz), 6.52 (1H, d, J=12.0 Hz), 6.42 (1H, s), 6.40 (1H d, J=12.0 Hz), 6.33 (1H, d, J=2.1 Hz), 6.27 (1H, t, J=2.1 Hz), 3.79 (3H, s, OCH$_3$), 3.67 (3H, s, OCH$_3$). Anal. (C$_{16}$H$_{16}$O$_3$) C, H. (E)-isomer (14h): EIMS m/z 256 (M+), 225, 181, 152, 115; IR (KBr, cm$^{-1}$) ν$_{max}$ 3405, 2936, 2837, 1593, 1510, 1456, 1252, 1150, 1057; and $^1$H-NMR δ 7.44 (2H, d, J=8.7 Hz), 7.02 (1H, d, J=15.9 Hz), 6.90 (2H, d, J=8.7 Hz), 6.86 (1H, d, J=15.9 Hz), 6.63 (1H, t, J=2.1 Hz), 6.58 (1H, t, J=2.1 Hz), 6.31 (1H, t, J=2.1 Hz), 3.83 (3H, s, OCH$_3$) 3.82 (3H, s, OCH$_3$).

In a like manner 3,5-di(tert-butyldimethylsilyloxy)-4'-methoxy-stilbene (14i and 14j) was obtained. Intermediate 9a and 3 served as starting material for preparing stilbene 14i (1.73 g) and 14j (0.19 g). (Z)-isomer (14i); EIMS m/z 470 (M+), 455, 413, 147, 73; IR (KBr, cm$^{-1}$) ν$_{max}$ 2955, 2859, 1582, 1510, 1437, 1331, 1254, 1165, 1031, 678; $^1$H-NMR δ 7.17 (2H, d, J=8.1 Hz), 6.75 (2H, d, J=8.1 Hz), 6.49 (1H, d, J=12.0 Hz), 6.39 (1H, d, J=12.0 Hz), 6.35 (2H, d, J=2.4 Hz), 6.19 (1H, t, J=2.4 Hz), 3.77 (3H, s, OCH$_3$), 0.93 (18H, s, C(CH$_3$)$_3$×2), 0.10 (12H, s, Si(CH$_3$)$_2$×2). Anal. (C$_{25}$H$_{42}$O$_3$Si$_2$) C, H. (E)-isomer (14j); EIMS m/z 470 (M+), 455, 413, 147, 73; IR (KBr, cm$^{-1}$) ν$_{max}$ 2955, 2859, 1582, 1510, 1437, 1331, 1254, 1165, 1031, 980; $^1$H-NMR δ 7.44 (2H, d, J=8.1 Hz), 6.97 (1H, d, J=16.2 Hz), 6.89 (2H, d, J=8.1 Hz), 6.83 (1H, d, J=16.2 Hz), 6.59 (2H, d, J=2.1 Hz), 6.24 (114, t, J=2.1 Hz), 3.83 (3H, s, OCH$_3$), 1.00 (18H, s, C(CH$_3$)$_3$×2), 0.22 (12H, s, Si(CH$_3$)$_3$×2).

The preceding silyloxy protected stilbene isomers (14i and j) were deprotected to yield 3,5-dihydroxy-4'-methoxy-stilbene (14k and l) 0.60 g and 0.05 g respectively. (Z)-isomer (14k); EIMS m/z 242 (M+), 226, 211, 194, 181, 152, 137, IR (KBr, cm$^{-1}$) $\nu_{max}$ 3356, 3009, 2971, 2837, 1605, 1510, 1254, 1154, 1005, 677; $^1$H-NMR δ 7.20 (2H, d, J=8.7), 6.77 (2H, d, J=8.7 Hz), 6.50 (1H, d, J=12.0 Hz) 6.36 (1H, d, J=12.0 Hz), 6.32 (2H, d, J=2.1 Hz), 6.22 (1H, t, J=2.1 Hz), 4.89 (2H, bs, OH×2), 3.77 (3H, s, OCH$_3$). Anal. (C$_{15}$H$_{14}$O$_3$) C, H. E-Isomer (14l); EIMS m/z 242, (M+), 226, 211, 194, 181, 152, 137; IR (KBr, cm$^{-1}$) $\nu_{max}$ 3356, 3009, 2971, 2837, 1605, 1510, 1254, 1154, 1005, 974; $^1$H-NMR δ 7.43 (2H, d, J=8.1 Hz), 7.01, (1H, d, J=15.9 Hz) 6.90 (2H, d, J=8.1 Hz), 6.83 (1H, d, J=15.9 Hz), 6.56 (2H, d, J=2.4 Hz), 6.25 (1H, t, J=2.4 Hz), 4.70 (2H, bs, OH×2), 3.83 (3H, s, OCH$_3$).

Then (Z)-3,5-dimethoxy-4-[O-bis(benzyl)phosphoryl]-stilbene (14m) was obtained as follows. A mixture of phenol 14c (3.9 g) and N,N-dimethylaminopyridine (0.2 g) in anhydrous acetonitrile (30 ml) was cooled to −10° C., and carbon tetrachloride (7.3 ml, 5 equiv.) and DIEA (5.5 ml, 2.1 equiv.) were added. The mixture was stirred at −10° C. for 30 minutes under argon, dibenzylphosphite (5.0 ml, 1.5 equiv.) was added, and the solution was stirred for 12 hours and then poured into 0.5 M monobasic potassium phosphate. The mixture was extracted with ethyl acetate and removal of solvent in vacuo from the organic phase yielded a tan oil. This was subjected to column chromatography (4:1 hexane:ethyl acetate), and the phosphate ester was recovered as a tan oil (6.6 g, 85%): EIMS m/z 516 (M+), 425, 334, 319, 255, 227, 91; IR (KBr, cm$^{-1}$) $\nu_{max}$ 3443, 3007, 2959, 2837, 1591, 1505, 1456, 1289, 1208, 1155, 1015, 953: $^1$H-NMR δ 7.32 (1 OH, m, AR—H), 7.19 (2H d, J=8.4 Hz), 7.01 (2H, d, J=8.4 Hz), 6.52 (2H, s, H$_{1a,1'a}$), 6.36 (2H, d, J=2.0 Hz), 6.31 (1H, t, J=2.0 Hz), 5.11 (2H, s, Bn), 5.08 (2H, s, Bn), 3.62 (6H, s, OCH$_3$×2); $^{13}$C-NMR (75.5 MHz) δ 160.6, 149.5, 149.5, 138.8, 135.4, 135.4, 134.2, 130.4, 130.3, 129.4, 128.6, 128.6, 128.0, 127.0, 119.8, 119.7, 106.6, 99.8, 70.0, 69.9, 55.2. Anal. (C$_{30}$H$_{29}$O$_6$P) C, H, P.

Sodium Resverastatin Phosphate (14n) was obtained as described below. To a solution of the dibenzyl phosphate (14m, 2.62 g) in anhydrous dichloromethane (15 ml) at 0° C. was added bromotrimethylsilane (1.40 ml, 2.1 equiv.), and the mixture was stirred for 2 hours. Water (10 ml) was added, the solution was stirred for 1 hour and then washed with ethyl acetate, and the aqueous phase was freeze-dried to a white solid. To a solution of the solid in ethanol (30 ml) was added sodium methoxide (0.57 g), and the suspension was stirred for 12 hours. Solvent was removed in vacuo and the resulting tan oil was dissolved in water. The solution was washed with ethyl acetate and then freeze-dried to afford 1.88 g of colorless solid (98%): HRFAB m/z; IR (KBr, cm$^{-1}$) $\nu_{max}$ 3385, 2999, 2938, 2834, 1601, 1508, 1366, 1155, 1063, 683; $^1$H-NMR δ 6.93 (2H, d, J=8.4 Hz), 6.85 (2H, d, J=8.4 Hz), 6.29 (1H, d, J=12.4 Hz), 6.17 (2H, s, H$_{2,6}$), 6.15 (1H, d, J=12.4 Hz), 6.09 (1H, s, H4), 3.34 (6H, s, OCH$_3$×2); $^{13}$C-NMR (75.5 MHz) δ 171.1, 160.1, 139.9, 131.8, 130.8, 130.0, 129.0, 120.3, 107.3, 99.7, 55.6.

The following general procedure was used for benzhydrol formation. To the bromide (1-10 mmol) in anhydrous tetrahydrofuran (5-35 ml) at −78° C. was added n-butyllithium (2.5 M, 1.1 equiv.) and the resulting solution stirred under argon for 15 minutes. A solution of aldehyde (1.0 equiv.) in tetrahydrofuran was added dropwise over 30 minutes and the mixture stirred for 6 hours. The solution was poured into water and extracted with ethyl acetate. The organic phase was washed with water and removal of the solvent in vacuo afforded an oil that was purified by flash column chromatography (9:1 hexane-ethyl acetate).

Reacting 4-bromoanisole (2.3 g) and 3,5-dimethoxybenzaldehyde (2.1 g) led to 15a (2.7 g, 80.9%) as a colorless oil: EIMS m/z 274 (M+) 257, 243, 227, 165, 139, 135, 109, 77; IR (KBr, cm$^{-1}$) $\nu_{max}$ 3451, 3001, 2940, 2837, 1597, 1248, 1172, 1034; $^1$H-NMR δ 7.28 (2H, d, J=8.8 Hz), 6.85 (2H, d, J=8.8 Hz), 6.53 (2H, d, J=2.0 Hz), 6.35 (1H, t, J=2.0 Hz), 5.72 (1H, d, J=2.8 Hz), 3.78 (3H, s, OCH$_3$), 3.76 (3H, s, OCH$_3$); $^{13}$C-NMR (75.5 MHz) δ 160.9, 159.1, 146.5, 135.9, 127.9, 113.9, 104.4, 99.3, 75.8, 55.3, 55.3. Anal. (C$_{16}$H$_{18}$O$_4$) C, H.

The following general procedure was followed for benzophenone formation. To a solution of the benzhydrol (1-10 mmol) in dichloromethane (5-35 ml) was added pyridinium dichromate (2.0 equiv.) and molecular sieves (4 Å activated powder, same weight as PDC), and the resulting suspension was stirred under argon for 24 hours. The reaction mixture was filtered through celite and the solvent removed in vacuo to yield a brown oil. The oil was subjected to gravity column chromatography (4:1 hexane-ethyl acetate) to yield the desired product in 75-90% yield.

Further, 3,4',5-trimethoxybenzophenone (16a) was obtained. Alcohol 15a (1.1 g) provided a solid (0.8 g, 77.7%) that recrystallized from methanol in colorless needles: m.p.=90.3-91.6° C. (lit.[21] m.p.=97-98° C.); EIMS m/z 272 (M$^+$), 257, 241, 229, 165, 135, 92, 77; IR (KBr, cm$^{-1}$) $\nu_{max}$ 3071, 2967, 2841, 1645, 1588, 1263, 1065; $^1$H-NMR δ 7.84 (2H, d, J=9.0 Hz), 6.95 (2H, d, J=9.0 Hz), 6.87 (2H, d, J=2.0 Hz), 6.65 (1H, t, J=2.0 Hz), 3.88 (3H, s, OCH$_3$), 3.82 (3H, s, OCH$_3$); $^{13}$C-NMR (75.5 MHz) δ 195.2, 163.3, 160.5, 140.2, 132.6, 130.1, 113.6, 107.6, 104.2, 55.6, Anal. (C$_{16}$H$_{16}$O$_4$) C, H.

Then 1-bromo-4-O-(tert-butyldimethylsilyloxy)benzene (17) was obtained. First, 4-bromophenol (4.15 g) was dissolved in anhydrous dichloromethane (40 ml), then imidazole (1.63 g) and tert-butyldimethylsilyl chloride (3.61 g) were added. The cream suspension was stirred under argon for 12 hours and the reaction was terminated with addition of water. The mixture was extracted with ethyl acetate. The organic phase was washed with water and the solvent was removed in vacuo to afford a yellow oil that was subjected to flash column chromatography (9:1 hexane:ethyl acetate) to yield a colorless oil (87%, 6.0 g): EIMS m/z 274 (M$^+$), 257, 243, 227, 165, 139, 135, 109, 77; IR (KBr, cm$^{-1}$) $\nu_{max}$ 2957, 2859, 1588, 1487, 1458, 910, 839; $^1$H-NMR δ 7.32 (2H, d, J=8.7 Hz), 6.71 (2H, d, J=8.7 Hz), 0.97 (9H, s, C(CH$_3$)$_3$), 0.18 (6H, s, Si (CH$_3$)$_2$). Anal (C$_{12}$H$_{19}$BrOSi) C, H.

Protected bromophenol 17 (3.2 g) and 3,5-dimethoxybenzaldehyde (1.8 g) afforded 15b as a colorless oil (3.4 g, 83%): EIMS m/z 374 (M$^+$), 317, 167, 151, 139; IR (KBr, cm$^{-1}$ $\nu_{max}$ 3420, 2957, 2859, 1607, 1260, 1155, 1063, 839; $^1$H-NMR δ 7.21 (2H, d, J=8.4 Hz), 6.80 (2H, d, J=8.4 Hz), 6.53 (2H, d, J=2.0 Hz), 6.36 (1H, t, J=2.0 Hz), 5.67 (1H, s), 3.75 (6H, s, OCH$_3$×2), 0.99 (9H, s, C(CH$_3$)$_3$), 0.20 (6H, s, Si(CH$_3$)$_2$); $^{13}$C-NMR (75.5 MHz) δ 160.7, 155.0, 146.5, 136.4, 127.8, 119.9, 104.4, 99.2, 75.7, 55.2, 25.6, 18.1, −4.5. Anal. (C$_{21}$H$_{30}$O$_4$Si) C, H.

Alcohol 15b (0.12 g) was deprotected with TBAF as for the stilbenes above to provide 4'-Hydroxy-3,5-dimethoxybenzhydrol 15c as a colorless oil (0.03 g, 42%): EIMS m/z 260 (M$^+$), 243, 165, 139, 121, 95; IR (KBr, cm$^{-1}$) $\nu_{max}$ 3362, 2932, 2932, 2859, 1599, 1256, 1155, 1067; $^1$H-NMR δ 7.16 (2H, d, J=8.4 Hz), 6.72 (2H, d, J=8.4 Hz), 6.52 (2H, d, J=2.4 Hz), 6.34 (1H, t, J=2.4 Hz), 5.66 (1H, s), 3.73 (6H, s, OCH$_3$× 2); $^{13}$C-NMR (75.5 MHz) δ 160.6, 155.4, 146.3, 135.3, 128.0, 115.3, 104.4, 99.2, 75.8, 55.3. Anal. (C$_{15}$H$_{16}$O$_4$) C, H.

Alcohol 15b (0.58 g) led to 4'-(tert-butyldimethylsilyloxy)-3,5-dimethoxybenzophenone 16b as a colorless oil (0.46 g, 80%): EIMS m/z 372 (M$^+$), 315, 165, 157, 137, 28; IR (KBr, cm$^{-1}$) $v_{max}$ 2957, 2859, 1657, 1260, 1067, 910, 841; $^1$H-NMR δ 7.78 (2H, d, J=9.2 Hz), 6.89 (2H, d, J=9.2 Hz), 6.87 (2H, t, J=2.0 Hz), 6.63 (1H, t, J=2.0 Hz), 3.80 (6H, s, OCH$_3$×2), 0.98 (9H, s, C(CH$_3$)$_3$), 0.23 (6H, s, Si(CH$_3$)$_2$); $^{13}$C-NMR (75.5 MHz) δ 195.0, 160.3, 159.8, 140.0, 132.3, 130.5, 119.6, 107.5, 104.1, 55.5, 25.6, 18.3, −4.3. Anal. (C$_{21}$H$_{28}$O$_4$Si) C, H.

The general procedure for benzophenone deprotection with TBAF is set forth below. To a solution of the protected phenol (0.3-3.5 mmol) in anhydrous tetrahydrofuran (5-25 ml) was added tetrabutylammonium fluoride (1 M, 1.0 equiv. per TBDMS), and the pale yellow solution was stirred for 45 minutes. The mixture was poured into water and extracted with ethyl acetate. Removal of the solvent in vacuo from the organic phase afforded a tan oil that was subjected to gravity column chromatography (9:1 hexane:ethyl acetate) to afford the product (70-93% yield).

Protected benzophenone 16b (0.71 g) led to 16c as a white solid (0.35 g, 72%): EIMS m/z 258 (M$^+$), 243, 227, 199, 165, 121, 45; IR (KBr, cm$^{-1}$) $v_{max}$ 3424, 2940, 1640, 1591, 1454, 1206, 1157, 1065; $^1$H-NMR δ 7.68 (2H, d, J=8.8 Hz), 6.80 (2H, d, J=8.8 Hz), 6.75 (2H, d, J=2.0 Hz), 6.53 (1H, t, J=2.0 Hz), 3.70 (6H, s, OCH$_3$×2); $^{13}$C-NMR (75.5 MHz) δ 196.0, 162.3, 160.4, 140.2, 133.1, 128.6, 115.6, 107.5, 104.2, 55.5. Anal. (C$_{15}$H$_{14}$O$_4$) C, H.

Combining 4-bromoanisole (0.43 g) and aldehyde 9a (0.76 g) provided 3,5-di-(tert-butyldimethylsilyloxy)-4'-methoxybenzhydrol 15d as a faint yellow oil (0.80 g, 82%): EIMS m/z 474 (M$^+$), 459, 417, 361, 343, 73; IR (KBr, cm$^{-1}$) $v_{max}$ 3420, 2932, 2859, 2361, 1591, 1451, 1252, 1163, 1026, 833; $^1$H-NMR δ 7.29 (2H, d, J=9.04 Hz), 6.89 (2H, d, J=9.0 Hz), 6.52 (2H, d, J=2.0 Hz), 6.28 (1H, t, J=2.0 Hz), 5.70 (1H, s), 3.83 (3H, s, OCH$_3$), 1.00 (18H, s, C(CH$_3$)$_3$×2), 0.20 (12H s, Si(CH$_3$)$_2$×2); $^{13}$C-NMR (75.5 MHz) δ 159.0, 156.5, 146.1, 136.0, 127.9, 113.7, 111.5, 111.0, 75.5, 55.3, 25.7, 18.2, −4.4. Anal. (C$_{26}$H$_{42}$O$_4$Si$_2$) C, H.

Alcohol 15d (0.72 g) provided 3,5-di-(tert-butyldimethylsilyloxy)-4'-methoxybenzophenone 16d as a colorless oil (0.64 g, 90%): EIMS m/z 472 (M$^+$), 457, 415, 359, 135, 73; IR (KBr, cm$^{-1}$) $v_{max}$ 2957, 2932, 2859, 1657, 1586, 1437, 1339, 1254, 1169, 831; $^1$H-NMR δ 7.82 (2H, d, J=9.0 Hz), 6.94 (2H, d, J=9.0 Hz), 6.80 (2H, d, J=1.5 Hz), 6.52 (1H, t, J=1.5 Hz), 3.88 (3H, s, OCH$_3$), 0.97 (18H, s, C(CH$_3$)$_3$×2), 0.19 (12H, s, Si(CH$_3$)$_2$×2); $^{13}$C-NMR (75.5 MHz) δ 195.0, 163.2, 156.3, 140.1, 132.5, 130.2, 115.6, 114.7, 113.5, 55.5, 25.7, 18.2, −4.4. Anal. (C$_{26}$H$_{40}$O$_4$Si$_2$) C, H.

Protected benzophenone 16d (0.54 g) led to 16e as a white solid (0.36 g, 93%): EIMS m/z 244 (M$^+$), 227, 135, 107, 92; IR (KBr, cm$^{-1}$) $v_{max}$ 3300, 2972, 2841, 2361, 1692, 1591, 1451, 1350, 1263, 1171, 1030; $^1$H-NMR δ 8.60 (2H, bs, OH×2), 7.80 (2H, d, J=9.0 Hz), 7.06 (2H, d, J=9.0 Hz), 6.69 (2H, d, J=2.5 Hz), 6.59 (1H, t, J=2.5 Hz), 3.91 (3H, s, OCH$_3$); $^{13}$C-NMR (75.5 MHz) δ 195.4, 164.6, 159.7, 141.8, 133.4, 131.5, 114.8, 109.3, 107.2, 56.4. Anal. (C$_{14}$H$_{12}$O$_4$) C, H.

Protected bromophenol 17 (0.49 g) and aldehyde 9a (0.62 g) afforded 15e as a faint yellow oil (0.76 g, 78%): EIMS m/z 574 (M$^+$), 559, 517, 461, 443, 73; IR (KBr, cm$^-$) $v_{max}$ 3420, 2932, 2859, 2361, 1591, 1451, 1252, 1163, 1026, 833; $^1$H-NMR δ 7.18 (2H, d, J=8.5 Hz), 6.79 (2H, d, J=8.5 Hz), 6.48 (2H, d, J=2.0 Hz), 6.25 (1H, t, J=2.0 Hz), 5.63 (1H, s, CH), 0.99 (9H, s, C(CH$_3$)$_3$), 0.97 (18H, s, C(CH$_3$)$_3$×2), 0.19 (6H, s, Si(CH$_3$)$_2$×2), 0.17 (12H, s, Si(CH$_3$)$_2$×2); $^{13}$C-NMR (75.5 MHz) δ 156.4, 155.0, 146.2, 136.7, 127.9, 119.9, 111.6, 111.0, 75.4, 25.7, 18.2, −4.4, −4.5. Anal. (C$_{31}$H$_{54}$O$_4$Si$_3$) C, H.

Alcohol 15e (0.50 g) led to 16f as a colorless oil (0.44 g, 89%): EIMS m/z 572 (M$^+$), 515, 459, 323, 193, 73; IR (KBr, cm$^{-1}$) $v_{max}$ 2932, 2861, 1661, 1589, 1437, 1339, 1256, 1167, 831; 1H-NMR δ 7.74 (2H, d, J=8.5 Hz), 6.88 (2H, d, J=8.5 Hz), 6.80 (2H, d, J=2.5 Hz), 6.52 (1H, t, J=2.5 Hz), 0.99 (9H, s, C(CH$_3$)$_3$), 0.97 (18H, s, C(CH$_3$)$_3$×2), 0.24 (6H, s, Si(CH$_3$)$_2$), 0.19 (12H, s, Si(CH$_3$)$_2$×2); $^{13}$C-NMR (75.5 MHz) δ 195.2, 159.9, 156.3, 140.0, 132.4, 130.7, 119.7, 115.7, 114.7, 25.7, 25.6, 18.3, 18.2, −4.4. Anal. (C$_{31}$H$_{52}$O$_4$Si$_3$) C, H.

Protected benzophenone 16f (0.42 g) led to 3,4',5-trihydroxybenzophenone 16g as a white solid (0.12 g, 73%): EIMS m/z 230 (M$^+$, 137, 121, 93, 65, 28; IR (KBr, cm$^-$) $v_{max}$ 3300, 2974, 1692, 1593, 1346, 1260, 1167; $^1$H-NMR δ 7.73 (2H, d, J=8.5 Hz), 6.95 (2H, d, J=8.5 Hz), 6.68 (2H, d, J=2.0 Hz), 6.57 (1H, t, J=2.0 Hz); $^{13}$C-NMR (75.5 MHz) δ 195.0, 162.4, 159.2, 141.6, 133.3, 130.2, 115.9, 108.8, 106.7. Anal. (C$_{13}$H$_{10}$O$_4$) C, H.

Protected bromophenol 17 (1.07 g) and aldehyde 9c (0.99 g) provided 15f as a faint yellow oil (1.19 g, 67%): EIMS m/z 474 (M$^+$), 459, 417, 361, 343, 73; IR (KBr, cm$^{-1}$) $v_{max}$ 3397, 2932, 2859, 1595, 1508, 1256, 1159, 839; $^1$H-NMR δ 7.19 (2H, d, J=8.4 Hz), 6.78 (2H, d, J=8.4 Hz), 6.55 (1H, s), 6.42 (1H, s), 6.29 (1H, s), 5.67 (1H, s, CH), 3.74 (3H, s, OCH$_3$), 0.96 (9H, s, C(CH$_3$)$_3$), 0.95 (9H, s, C(CH$_3$)$_3$), 0.17 (6H, s, Si(CH$_3$)$_2$), 0.15 (6H, s, Si(CH$_3$)$_2$); $^{13}$C-NMR (75.5 MHz) δ 160.5, 156.6, 155.0, 146.2, 136.4, 127.8, 119.9, 110.8, 105.1, 105.0, 75.7, 55.3, 25.7, 18.3), −4.3. Anal. (C$_{26}$H$_{42}$O$_4$Si$_2$) C, H.

Alcohol 15f (0.91 g) led to 16h as a colorless oil (0.71 g, 78%): EIMS m/z 472 (M$^+$), 415, 223, 193, 179, 73; IR (KBr, cm$^{-1}$) $v_{max}$ 2932, 2859, 1659, 1595, 1507, 1258, 1163, 839; $^1$H-NMR δ 7.76 (2H, d, J=8.8 Hz), 6.90 (1H, t, J=2.4 Hz), 6.88 (2H, d, J=8.8 Hz), 6.77 (1H, t, J=2.4 Hz), 6.58 (1H, t, J=2.4 Hz), 3.80 (3H, s, OCH$_3$), 0.99 (9H, s, C(CH$_3$)$_3$), 0.97 (9H, s, C(CH$_3$)$_3$), 0.24 (6H, s, Si(CH$_3$)$_2$), 0.20 (6H, s, Si(CH$_3$)$_2$); $^{13}$C-NMR (75.5 MHz) δ 195.0, 160.3, 159.8, 156.3, 140.0, 132.3, 130.6, 119.6, 114.2, 110.1, 107.6, 55.5, 25.7, 25.7, 18.3, 18.3, −4.3. Anal. (C$_{26}$H$_{40}$O$_4$Si$_2$) C, H.

Protected benzophenone 16h (0.61 g) led to 3,4'-dihydroxy-5-methoxybenzophenone 16i as a white solid (0.26 g, 82%): mp 179-180° C.; EIMS m/z 244 (M$^+$), 229, 213, 151, 121, 93; IR (KBr, cm$^{-1}$) $v_{max}$ 3333, 2961, 2841, 1690, 1589, 1435, 1346, 1165, 1059, 849; $^1$H-NMR δ 9.21 1H bs, OH), 8.66 (1H, bs, OH), 7.75 (2H, d, J=9.0 Hz), 6.96 (2H, d, J=9.0 Hz), 6.77 (2H, t, J=2.0 Hz), 6.74 (1H, t, J=2.0 Hz), 6.63 (1H, t, J=2.0 Hz), 3.80 (3H, s, OCH$_3$); $^{13}$C-NMR (75.5 MHz) δ 195.0, 162.6, 161.8, 159.2, 141.6, 133.4, 130.1, 116.0, 109.9, 107.0, 105.50, 55.8. Anal. (C$_{14}$H$_{12}$O$_4$) C, H.

Combining 4-bromoanisole (0.59 g) and aldehyde 9c (0.82 g) provided compound 15g as a faint yellow oil (0.59 g, 52%): EIMS m/z 374 (M$^+$), 359, 317, 299, 243, 75; IR (KBr, cm$^{-1}$) $v_{max}$ 3418, 2932, 2859, 1595, 1462, 1250, 1157, 1036, 837; $^1$H-NMR δ 7.30 (2H, d, J=8.4 Hz), 6.89 (2H, d, J=8.4 Hz), 6.58 (1H, s), 6.49 (1H, s), 6.32 (1H, s), 5.72 (1H, s, CH), 3.82 (3H, s, OCH$_3$), 3.77 (3H, s OCH$_3$), 0.99 (9H, s, C(CH$_3$)$_3$), 0.20 (6H, s, Si(CH$_3$)$_2$); $^{13}$C-NMR (75.5 MHz) δ 160.5, 158.9, 156.6, 146.2, 135.9, 127.8, 113.8, 110.7, 105.1, 104.9, 75.6, 55.3, 25.8, 18.3, −4.3. Anal. (C$_{21}$H$_{30}$O$_4$Si) C, H.

Alcohol 15g (0.54 g) led to colorless oil 3'-(tert-butyldimethylsilyloxy)-4',5-dimethoxybenzophenone 16j (0.41 g, 76%): EIMS m/z 372 (M$^+$), 315, 272, 135; IR (KBr, cm$^{-1}$) $v_{max}$ 2932, 2859, 1657, 1593, 1454, 1429, 1339, 1254, 1161, 1034, 839; $^1$H-NMR δ 7.83 (2H, d, J=8.8 Hz), 6.95 (2H, d, J=8.8 Hz), 6.89 (1H, t, J=1.2 Hz), 6.77 (1H, t, J=1.6 Hz), 6.58 (1H, t, J=2.2 Hz), 3.88 (3H, s, OCH$_3$), 3.80 (3H, s, OCH$_3$), 0.97 (9H, s, C(CH$_3$)$_3$), 0.20 (6H, s, Si(CH$_3$)$_2$); $^{13}$C-NMR (75.5 MHz) δ 194.9, 163.1, 160.4, 156.3, 140.1, 132.5, 130.0, 114.2, 113.4, 110.1, 107.6, 55.6, 55.5, 25.7, 18.1, −4.3. Anal. ($C_{21}H_{28}O_4Si$) C, H.

Protected benzophenone 16j (0.37 g) led to 4',5-dimethoxy-3-hydroxybenzophenone 16k as a colorless solid (0.18 g, 70%): EIMS m/z 258 (M⁺), 227, 135, 92, 77; IR (KBr, $cm^{-1}$) $v_{max}$ 3354, 3005, 2938, 2841, 1692, 1636, 1593, 1433, 1346, 1256, 1171, 1030; $^1$H-NMR δ 8.67 (1H, bs, OH), 7.80 (2H, dd, J=6.8, 2.0 Hz), 7.05 (2H, dd, J=6.8, 2.0 Hz), 6.77 (1H, dd, J=2.0, 1.6 Hz), 6.74 (1H, dd, J=2.4, 1.2 Hz), 6.64 (1H, t, J=2.4 Hz), 3.90 (3H, s, $OCH_3$), 3.80 (3H, s, $OCH_3$); $^{13}$C-NMR (75.5 MHz) δ 194.6, 164.0, 161.5, 159.0, 141.1, 132.8, 130.8, 114.3, 109.7, 106.9, 105.4, 55.9, 55.7. Anal. ($C_{15}H_{14}O_4$) C, H.

The following results lead to some observations. Because of the interesting biological properties of resveratrol (1), combined with the remarkable in vivo anticancer activity of combretastatin A-4 (2a) and its sodium phosphate prodrug (2b), a series of resveratrol structural modifications were investigated as an extension of applicant's combretastatin and phenstatin (2c) SAR research. (Ndayikengurukiye, H., et al., Alkoxylated p-phenylenevinylene Oligomers: Synthesis and Spectroscopic and Electrochemical Properties, *Tetrahedron* 1997, 53, 13811-13828.) Suitable application of the experimental procedures already developed for synthesis of combretastatin A-4 and its prodrug derivatives was extended to obtaining the cis and trans stilbenes as well as the benzophenones. (Pettit, G. R., et al., Antineoplastic agents 291. Isolation and synthesis of Combretastatin A04, A-5, and A-6, *J. Med. Chem.* 1995, 38, 1666-1672; Pettit, G. R., et al., Antineoplastic agents 443. Synthesis of the Cancer Cell Growth inhibitor Hydocyphenstatin and its Sodium Diphosphate Prodrug, *J. Med. Chem.* 2000, 43, 2731-2727.)

The cytotoxicity data from the resveratrol stilbenes was determined. The cis-isomer of resveratrol (1b) exhibited slightly less inhibitory effects on the cancer cell lines tested than did the trans-isomer. The trimethoxy stilbenes 4a,b are between 10-100 fold more active against tumor cell lines than the parent compound resveratrol (1), with compound 4a (the cis-stilbene) far more active than 4b.

Demethylation at any position yielded much less cytotoxic compounds than 4a, but the cis-stilbenes 14c, 14g and 14k all retained anticancer activity comparable to that of resveratrol. The corresponding trans-isomers 14d, 14h and 14l were all slightly less active than their cis counterparts.

Previous work by applicant had found that phenstatin (2c) retained most of the cytotoxic properties of combretastatin A-4 (2a); this suggested that the properties of compound 16a, as well as additional benzophenones might possibly be worthy of further investigation. (Pettit, G. R., et al., Antineoplastic Agents. 379. Synthesis of Phenstatin Phosphate, *J. Med. Chem.* 1998, 41, 1688-1695.) While the cytotoxic properties of most of these compounds were quite similar to those of the stilbene derivatives of resveratrol the trimethoxy derivative was again the most potent of the series. However, it was 10-100-fold less active than compound 4a, the analogous cis-stilbene.

General conclusions arising from the structure-activity relationship study of resveratrol based on cytotoxic effects on P-388 and human tumor cell lines can be summarized as: 3,4',5-$OCH_3$>>resveratrol, 4'-OH, prodrug, 3-OH>3,5-OH,3, 4'-OH>>3,4',5-OH. The trimethoxy derivatives (4a,b,16a) were all superior in activity to resveratrol (1) as well as the remaining variations. Resveratrol (1), however, was comparable in activity to several of the other cis-stilbenes described here, including the 4'-hydroxy (14g) and the 3-hydroxy (14c) cis-derivatives.

For this reason the synthesis of the prodrug of the 4'-hydroxystilbene 14c and the 3-hydroxystilbene 14g was attempted. The synthesized prodrug 14n was essentially identical to 14c in its effects on the growth of cancer cells. From the known antimitotic activity of combretastatin A-4 (2a) and phenstatin (2c) and their potent interactions with tubulin, it seemed possible that the most cytotoxic compounds prepared in the current series would also inhibit this important cellular protein.

Several of the newly synthesized compounds were therefore examined for inhibitory effects on tubulin assembly, in a direct comparison with 2a and 2c. Compound 4a proved to be more inhibitory than 2a, while, in contrast, 16a was somewhat less potent than 2c. Resveratrol (1) was inactive as an inhibitor of tubulin assembly. Compound 14c, representing demethylation at position 3 of 4a, was 16-fold less active than 4a.

Combretastatin A-4 (2a) binds in the colchicine site of tubulin and is exceptionally potent as an inhibitor of the binding of radiolabeled colchicine to tubulin. (Lin, C. M., et al., Antimitotic natural products Combretastatin A-4 and Combretastatin A-2: Studies on the Mechanism of Their Inhibition of the Binding of Colchicine to Tubulin, *Biochem.* 1989, 28, 6984-6991.) The two new active compounds, 4a and 4c, were compared to 2a and phenstatin (2c) for their effects on colchicine binding to tubulin. Combretastatin A-4 (2a) displayed its usual potency, inhibiting colchicine binding by 98% when the two drugs were present in equimolar (5 μM) concentrations and by 91% when 2a was present at 2 μM (the tubulin concentration in these experiments was 1.0 μM).

Compound 4a was essentially equivalent to 2a as an inhibitor of colchicine binding. Phenstatin (2c), despite its greater inhibition of polymerization, was less potent than combretastatin A-4 (2a) as an inhibitor of colchicine binding, while 16a had the least activity in both assays. The reasons for these discrepancies are at present unknown but do not appear to derive from salt or temperature differences in the reaction condition.

There is also some indication that Resveratrol (1) contained in the roots of *Polygonum cuspidatum* has apparently been used in Chinese and Japanese traditional medicine as a treatment for gonorrhea (Kubo, M., et al., *Shoyayugaku Zasshi* 1981, 35, 58.) In the present study, its activity against the etiologic agent of gonorrhea, *Neisseria gonorrhoeae*, was demonstrated in broth microdilution assays (Table IV). Stilbene production has been correlated with the resistance of grape leaves to fungal infection. (Langcake, R., et al., The Relationship of Resveratrol Production to Infection of Grapevine Leaves by *Botrytis cenerea, Vitis* 1979 18:244-253.) Most of the stilbenes evaluated for antimicrobial action had antifungal activity (Table IV). The dimethyl derivative of cis-resveratrol (14c), with both antibacterial and antifingal activities, was the most active of the stilbenes and benzophenones tested (Table IV). Further biological evaluation of such resveratrol structural modifications should include chemopreventive potential targets such as COX-1 and COX-2.

TABLE I

Cytotoxicity Data of Resveratrol (1), Combretastatin A-4 (2a), Resverastatin (14c), the Disodium Resverastatin Prodrug (14n) and Related Stilbenes.

| Compound | Leukemia P388 ED$_{50}$μg/mL | Pancreas-a BXPC-3 | Breast MCF-7 | CNS SF-268 GI$_{50}$μg/mL | Lung-NSC NCI-H460 | Colon KM201.2 | Prostate DU-145 |
|---|---|---|---|---|---|---|---|
| 1 | 4.49 | 3.3 | 3.9 | 4.1 | 3.6 | 13.1 | 3.5 |
| 1b | 24.4 | 15.5 | 14.8 | 5.0 | 13.2 | 22.0 | 10.2 |
| 2a | $3.0 \times 10^{-4}$ | 0.39 | — | $>1.0 \times 10^{-2}$ | $6.0 \times 10^{-4}$ | 0.34 | $8.0 \times 10^{-4}$ |
| 4a | $2.62 \times 10^{-2}$ | $3.4 \times 10^{-3}$ | — | $4.4 \times 10^{-3}$ | $2.8 \times 10^{-3}$ | — | $5.4 \times 10^{-3}$ |
| 4b | 2.77 | $3.5 \times 10^{-1}$ | — | $5.6 \times 10^{-1}$ | $6.2 \times 10^{-1}$ | — | 1.5 |
| 14c | 2.95 | 12.6 | 3.0 | 2.2 | 2.8 | 11.9 | 2.3 |
| 14d | 4.87 | 6.5 | 2.3 | 4.3 | 2.7 | 3.4 | 2.7 |
| 14g | 3.82 | 3.3 | — | 1.5 | $7.2 \times 10^{-1}$ | 2.6 | 2.5 |
| 14h | 31.5 | 12.7 | — | 10.3 | 11.2 | 13.1 | 6.0 |
| 14k | 2.75 | 14.1 | 12.7 | 15.6 | 6.4 | 17.7 | 10.6 |
| 14l | 28.9 | 6.3 | 3.4 | 3.1 | 6.8 | 3.8 | 2.7 |
| 14m | 4.45 | 5.4 | 9.0 | 38.5 | 10.7 | 24.7 | 35.6 |
| 14n | 2.81 | 6.6 | $7.3 \times 10^{-1}$ | 1.9 | 3.6 | 11.8 | 3.7 |

TABLE II

Cytotoxicity Data of Resveratrol (1), Phenstatin (2c) and Related Benzophenones and Benzhydrols.

| Compound | Leukemia P388 ED$_{50}$μg/mL | Pancreas-a BXPC-3 | Breast MCF-7 | CNS SF-268 GI$_{50}$μg/mL | Lung-NSC NCI-H460 | Colon KM201.2 | Prostate DU-145 |
|---|---|---|---|---|---|---|---|
| 1 | 4.49 | 3.3 | 3.9 | 4.1 | 3.6 | 13.1 | 3.5 |
| 2c | $3.3 \times 10^{-3}$ | — | — | $5.2 \times 10^{-2}$ | $5.7 \times 10^{-3}$ | $4.0 \times 10^{-2}$ | ND |
| 15a | 20.2 | 16.1 | — | 23.3 | 21.7 | 21.0 | 23.2 |
| 16a | 1.23 | $4.2 \times 10^{-1}$ | — | $8.6 \times 10^{-1}$ | $5.3 \times 10^{-1}$ | $4.2 \times 10^{-1}$ | 1.2 |
| 15c | >10 | 1.3 | 2.0 | $6.5 \times 10^{-1}$ | 2.3 | 5.3 | 5.8 |
| 16c | 24.8 | 4.0 | 2.2 | 3.8 | 3.0 | 3.6 | 4.1 |
| 16a | 17.8 | 21.2 | 21.7 | 24.5 | 16.6 | 24.5 | 15.1 |
| 16g | >100 | 20.5 | 30.6 | 22.3 | 25.0 | 24.5 | 15.0 |
| 16i | 26.2 | 21.7 | 26.8 | 26.4 | 12.1 | 31.6 | 16.5 |
| 16k | 13.4 | 15.0 | 14.2 | 13.9 | 10.3 | 16.2 | 12.6 |

TABLE III

Interactions of stilbenes and benzophenones with tubulin.

| Compound | Inhibition of tubulin Polymerization IC$_{50}$ (μM) ± SD | Inhibition of colchicine binding % Inhibition | |
|---|---|---|---|
| | | 2 μM inhibitor | 5 μM inhibitor |
| Resveratrol (1) | >40 | | |
| Combretastatin A-4 (2a) | 2.0 ± 0.2 | 91 ± 3 | 98 ± 1 |
| Phenstatin (2c) | 1.1 ± 0.1 | 73 ± 1 | 85 ± 2 |
| 4a | 1.8 ± 0.3 | 88 ± 1 | 95 ± 1 |
| Resverastatin (14c) | 29 ± 9 | | |
| 16a | 2.6 ± 0.3 | 47 ± 5 | 69 ± 0.3 |

The tubulin polymerization assay was performed as previously described.[24] The tubulin concentration was 10 μM, with varying drug concentrations, as required, to obtain $IC_{50}$ values. Extent of assembly after 20 min at 30° C. was the parameter measured. The colchicine binding assay was performed as earlier reported.[27] The tubulin concentration was 1.0 μM, the [3H] colchicine concentration was 5.0 μM, and the potential inhibitor concentrations were as indicated. Binding of colchicine was measured following a 10 min incubation at 37° C.

TABLE IV

| | Antimicrobial activities of resveratrol (1) and related stilbenes and benzophenones | | | | | | | | | | | |
|---|---|---|---|---|---|---|---|---|---|---|---|---|
| | Minimum inhibitory concentration (μg/ml) | | | | | | | | | | | |
| Microorganism | 1 | 4a | 14c | 14h | 14k | 14n | 15c | 16a | 16c | 16e | 16g | 16l | 16k |
| *Cryptococcus neoformans* | * | * | 16 | 16 | * | 64 | * | * | * | * | * | * | 64 |
| *Candida albicans* | * | * | 64 | * | * | * | * | * | * | * | * | * | * |
| *Staphylococcus aureus* | * | * | 32 | * | * | * | * | * | * | * | * | * | * |
| *Streptococcus pneumoniae* | * | * | 16 | * | * | * | 16 | * | 64 | * | 64 | 64 | 32-64 |
| *Enterococcus faecalis* | * | * | 32-64 | * | * | * | * | * | * | * | * | * | * |
| *Micrococcus luteus* | * | * | 8 | 16-64 | * | 32-64 | * | * | * | * | * | * | * |
| *Escherichla coli* | * | * | * | * | * | * | * | * | * | * | * | * | * |
| *Enterococcus faecalis* | * | * | * | * | * | * | * | * | * | * | * | * | * |
| *Enterobacter cloacae* | * | * | * | * | * | * | * | * | * | * | * | * | * |
| *Stenotrophomonas maltophilia* | * | * | * | * | * | * | * | * | * | * | * | * | * |
| *Neisseria gonorrhoeae* | 16-32 | * | 8 | 8 | 16 | 8-32 | 2-4 | 32 | 32-64 | * | * | 32 | 16-32 |

*, no inhibition at 64 μg/ml

What is claimed is:

1. A method for synthesizing the compound 14g having the following structure and wherein $R_1$=—OH and $R_2$=$R_3$=—$OCH_3$:

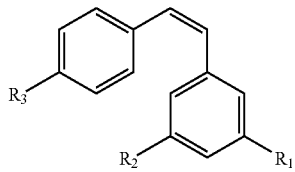

comprising the following steps:
(a) protecting 3,5-dihydroxybenzaldehyde by reacting it in dimethylformamide with DIEA and silyl chloride;
(b) separating the products of step (a) to obtain 3-(tert-butyldimethylsilyloxy)-5-hydroxybenzaldehyde;
(c) adding to the 3-(tert-butyldimethylsilyloxy)-5-hydroxybenzaldehyde obtained in step (b) molecular sieves, proton sponge and trimethyloxonium tetrafluoroborate, then stirring, then filtering, then rinsing sieves with ethyl acetate, then removing the ethyl acetate containing solvent from the filtrate to yield an oil;
(d) purifying the oil produced in step (c), to yield 3-(tert-butyldimethylsilyloxy)-5-methoxybenzaldehyde;
(e) reacting the 3-(tert-butyldimethylsilyloxy)-5-methoxybenzaldehyde produced in step (d) with 4-(tert-butyldiphenylsilyloxy)-benzyltriphenyl phosphonium bromide to produce (Z)- and (E)-3-(tert-butyldimethylsilyloxy)-5,4'-dimethoxy-stilbene; and
(f) deprotecting, and then separating, the product of step (e), to obtain compound 14g.

2. A method for synthesizing the compound 14c having the following structure wherein $R_4$=$R_5$=—$OCH_3$ and $R_6$=—OH:

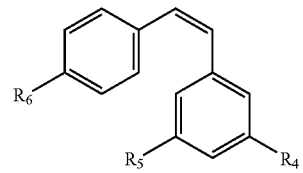

comprising the following steps:
(a) protecting 4-hydroxybenzaldehyde by reaction with Hunig's base to obtain a solution of 4-(tert)-butyldimethylsilyloxy-benzaldehyde;
(b) adding tert-butyldimethylsilylchloride to the solution formed in step (a);
(c) pouring the reaction mixture of step (b) into water, extracting with solvent, and removing solvent in vacuo to recover 4-(tert)-butyldimethylsilyloxy-benzaldehyde;
(d) reacting the 4-(tert)-butyldimethylsilyloxy-benzaldehyde obtained in step (c) with 3,5-dimethoxybenzyltriphenyl phosphonium bromide and n-butyl lithium in tetrahydrofuran to form (Z)- and (E)-4'-(tert-butyldimethylsilyloxy)-3,5-dimethoxy-stilbene;
(e) separating the (Z) and (E) isomers of the 4'-(tert-butyldimethylsilyloxy)-3,5-dimethoxy-stilbene formed in step (d) to obtain (Z)-4'-(tert-butyldimethylsilyloxy)-3,5-dimethoxy-stilbene;
(f) reacting the (Z)-4'-(tert-butyldimethylsilyloxy)-3,5-dimethoxy-stilbene in anhydrous tetrahydrofuran with tetrabutylammonium fluoride; and
(g) separating the products of step (f) to obtain compound 14c.

3. A method for synthesizing the compound 14k having the following structure wherein $R_7=R_8=$—OH and $R_9=$—$OCH_3$:

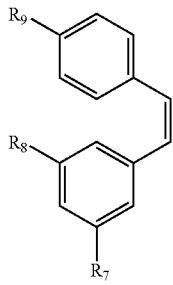

comprising the following steps:
(a) reacting 4-methoxybenzyltriphenylphosphonium bromide and 3,5-di(tert-butyldimethylsilyloxy)-benzaldehyde to obtain (Z)- and (E)-3,5-di(tert-butyldimethylsilyloxy)-4'-methoxy-stilbene);
(b) deprotecting the (Z)- and (E)-3,5-di(tert-butyldimethylsilyloxy)-4'-methoxy-stilbene obtained in step (a); and
(c) separating the product of step (b) to obtain compound 14k.

4. A method for synthesizing compound 14m, the resveratrol derivative having the following formula wherein $R_{10}=R_{11}=$—$OCH_3$ and $R_{12}=$—$O(PO)(OBn)_2$,

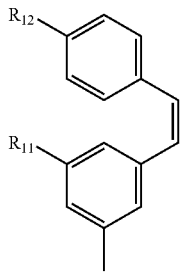

comprising the following steps:
(a) protecting 4-hydroxybenzaldehyde with Hunig's base to obtain a solution of 4-(tert)-butyldimethylsilyloxy-benzaldehyde;
(b) adding tert-butyldimethylsilylchloride to the solution formed in step (a);
(c) pouring the solution formed in step (b) into water, extracting with solvent, and removing solvent in vacuo to recover 4-(tert)-butyldimethylsilyloxy-benzaldehyde;
(d) reacting the 4-(tert)-butyldimethylsilyloxy-benzaldehyde obtained in step (c) with phosphonium bromide and n-butyl lithium in tetrahydrofuran to form (Z)- and (E)-4'-(tert-butyldimethylsilyloxy)-3,5-dimethoxy-stilbene;
(e) separating the (Z) and (E) isomers of the 4'-(tert-butyldimethylsilyloxy)-3,5-dimethoxy-stilbene to obtain (Z)-4'-(tert-butyldimethylsilyloxy)-3,5-dimethoxy-stilbene;
(f) reacting the (Z)-4'-(tert-butyldimethylsilyloxy)-3,5-dimethoxy-stilbene obtained in step (e) with tetrabutylammonium fluoride and stirring, and separating the product of step (f) to obtain (Z)-3,5-dimethoxy-4'-hydroxy-stilbene;
(g) forming, then cooling, a mixture of (Z)-3,5-dimethoxy-4'-hydroxy-stilbene obtained from step (f) and N,N-dimethylaminopyridine in anhydrous acetonitrile;
(h) adding carbon tetrachloride and DIEA and to the cooled mixture of step (g), and stirring;
(i) pouring the product of step (h) into monobasic potassium phosphate, extracting with solvent and then removing solvent in vacuo to yield an organic phase; and
(j) subjecting the organic phase from step (i) to separation to obtain compound 14m.

5. A method for synthesizing compound 14n, the resveratrol derivative having the following formula wherein $R_{10}=R_{11}=$—$OCH_3$ and $R_{12}=$—$O(PO)(ONa)_2$,

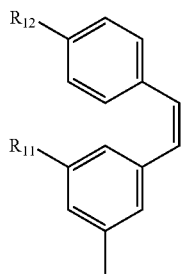

comprising the following steps:
(a) protecting 4-hydroxybenzaldehyde with Hunig's base to obtain a solution of 4-(tert)-butyldimethylsilyloxy-benzaldehyde;
(b) adding tert-butyldimethylsilylchloride to the solution formed in step (a);
(c) pouring the solution formed in step (b) into water, extracting with solvent, and removing solvent in vacuo to recover 4-(tert)-butyldimethylsilyloxy-benzaldehyde;
(d) reacting the 4-(tert)-butyldimethylsilyloxy-benzaldehyde obtained in step (c) with phosphonium bromide and n-butyl lithium in tetrahydrofuran to form (Z)- and (E)-4'-(tert-butyldimethylsilyloxy)-3,5-dimethoxy-stilbene;
(e) separating the (Z) and (E) isomers of the 4'-(tert-butyldimethylsilyloxy)-3,5-dimethoxy-stilbene to obtain (Z)-4'-(tert-butyldimethylsilyloxy)-3,5-dimethoxy-stilbene;
(f) reacting the (Z)-4'-(tert-butyldimethylsilyloxy)-3,5-dimethoxy-stilbene obtained in step (e) with tetrabutylammonium fluoride and stirring, and separating the product of step (f) to obtain (Z)-3,5-dimethoxy-4'-hydroxy-stilbene;
(g) forming, then cooling, a mixture of (Z)-3,5-dimethoxy-4'-hydroxy-stilbene obtained from step (f) and N,N-dimethylaminopyridine in anhydrous acetonitrile;
(h) adding carbon tetrachloride and DIEA and to the cooled mixture of step (g), and stirring;
(i) pouring the product of step (h) into monobasic potassium phosphate, extracting with solvent and then removing solvent in vacuo to yield an organic phase;
(j) subjecting the organic phase from step (i) to separation to obtain (Z)-3,5-dimethoxy-4-[O-bis(benzyl)phosphoryl]-stilbene;

(k) adding bromotrimethylsilane to a solution of the (Z)-3,5-dimethoxy-4-[O-bis(benzyl)phosphoryl]-stilbene obtained in step (j) in anhydrous dichloromethane, and stirring;

(l) adding water to the stirred solution obtained in step (k), washing with solvent to form an aqueous phase, then freeze drying the aqueous phase to form a solid;

(m) forming a solution of the solid formed in step (l) and a solvent, adding sodium methoxide to the solution, stirring, removing the solvent; and (n) recovering a solid remaining after step (m) to obtain compound 14n.

\* \* \* \* \*